(12) United States Patent
Chang et al.

(10) Patent No.: US 10,131,903 B2
(45) Date of Patent: Nov. 20, 2018

(54) MICROFLUIDIC PLATFORM FOR SYNTHETIC BIOLOGY APPLICATIONS

(75) Inventors: Chieh Chang, San Jose, CA (US); Rajiv Bharadwaj, Emeryville, CA (US); Anup K. Singh, Danville, CA (US); Aarthi Chandrasekaran, San Jose, CA (US); Nathan J. Hillson, San Francisco, CA (US)

(73) Assignees: The Regents of the University of California, Oakland, CA (US); Sandia Corporation, Livermore, CA (US)

( * ) Notice: Subject to any disclaimer, the term of this patent is extended or adjusted under 35 U.S.C. 154(b) by 0 days.

(21) Appl. No.: 13/437,727

(22) Filed: Apr. 2, 2012

(65) Prior Publication Data

US 2012/0258487 A1    Oct. 11, 2012

Related U.S. Application Data

(60) Provisional application No. 61/471,027, filed on Apr. 1, 2011.

(51) Int. Cl.
| | | |
|---|---|---|
| *C12P 19/34* | (2006.01) | |
| *C12N 15/10* | (2006.01) | |
| *C12N 15/66* | (2006.01) | |
| *C12N 15/00* | (2006.01) | |
| *C12P 21/06* | (2006.01) | |

(52) U.S. Cl.
CPC ......... *C12N 15/1027* (2013.01); *C12N 15/10* (2013.01); *C12N 15/66* (2013.01)

(58) Field of Classification Search
None
See application file for complete search history.

(56) References Cited

U.S. PATENT DOCUMENTS

| 8,454,906 B2 * | 6/2013 | Mathies et al. ............... 422/505 |
| 2007/0281309 A1 | 12/2007 | Kong et al. |
| 2009/0142236 A1 * | 6/2009 | Unger et al. .................. 422/130 |
| 2011/0124049 A1 | 5/2011 | Li et al. |

FOREIGN PATENT DOCUMENTS

WO    2008/024319 A2 *  2/2008  ............. B01J 19/00

OTHER PUBLICATIONS

Lee et al., "A Functional Analysis of the Spacer of V(D)J Recombination Signal Sequences" 1(1) PLoS One 56-69 (2003).*
Hong et al., "Molecular biology on a microfluidic chip" 18 Journal of Physics: Condensed Matter S691-S701 (2006).*
Engler et al., "Golden Gate Shuffling: A One-Pot DNA Shuffling Method Based on Type IIs Restriction Enzymes" 4(5) PLoS One e5553 (2009).*
Dittrich et al., "An Integrated Microfluidic System for Reaction, High-Sensitivity Detection, and Sorting of Fluorescent Cells and Particles" 75 Analytical Biochemistry 5767-5774 (2003).*
Davis, "ApE A plasmid Editor" 2013.*
Cold Spring Harbor Press Sample Protocol (pp. 55-57) (2006).*
Ellis et al., "DNA assembly for synthetic biology: from parts to pathways and beyond" 3 Integrative Biology 109-118 (Jan. 19, 2011).*
Pal et al., "An integrated microfluidic device for influenza and other genetic analyses" 5 Lab on a Chip 1024-1032 (2005).*
Dagani et al. (2007) "Microfluidic self-assembly of live *Drosophila* embryos for versatile high-throughput analysis of embryonic morphogenesis." *Biomed Microdevices* 9(5):681-94 [DOI 10.1007/s10544-007-9077-z].

* cited by examiner

*Primary Examiner* — Nancy J Leith
(74) *Attorney, Agent, or Firm* — Tom Hunter; Weaver Austin Villeneuve & Sampson LLP

(57) ABSTRACT

This invention provides methods and compositions for assembling biological constructs (e.g., plasmids, transformed cells, etc.). In certain embodiments the methods involve encapsulating separate components of the biological construct each in a fluid droplet confined in a fluid channel; optionally mixing droplets from different fluid channels to form a sequenced order of droplets carrying different components of the biological construct in a channel or chamber; and optionally combining two or more droplets each containing different components of the biological construct to permit the components to react with each other in one or more reactions contributing to the assembly of the biological construct.

13 Claims, 49 Drawing Sheets

Droplet-based Microfluidic Chip

Two-phase system: air/water, oil/water
Droplet-based microfluidics
- Discreet nano/pico-liter reactors
- Minimal cross-talk
- Large-scale integration
- Reagent savings
- Efficient use of chip real-estate
- Merging/mixing/reaction/incubation of reagent droplets enables flexible bioanalysis system

Droplet Generation and Queuing

1

MICROFLUIDIC PLATFORM FOR SYNTHETIC BIOLOGY APPLICATIONS

CROSS-REFERENCE TO RELATED APPLICATIONS

This application claims benefit of and priority to U.S. Ser. No. 61/471,027, filed on Apr. 1, 2011, which is incorporated herein by reference in its entirety for all purposes.

STATEMENT OF GOVERNMENTAL SUPPORT

This invention was made with government support under Contract No. DE-AC02-05CH11231 awarded by the U.S. Department of Energy. The government has certain rights in this invention.

FIELD OF THE INVENTION

The present invention relates to synthetic biology and microfluidics. In certain embodiments microfluidic devices and methods are provided for the synthesis of biological constructs including, but not limited to plasmids, and transformed cells.

BACKGROUND OF THE INVENTION

Synthetic biology applications often involve assembly of several biological parts (e.g., genes) in a plasmid. This can lead to a large combinatorial problem where several thousands of combinations of parts have to be assembled. The scale of the problem is a significant challenge in terms of cost and time required to generate all the possible combinations. Currently, a combination of 96/384 well plates and manual pipetting or very expensive robotics instrumentation is used to perform parts assembly and screening.

SUMMARY OF THE INVENTION

Methods and devices are provided for assembling (and optionally screening) biological constructs (e.g., plasmids, transformed cells, etc.). In certain embodiments the devices encapsulate one or more components of the biological construct in droplets in a microfluidics system. The system then orders and sequences the combination and/or reaction of the components to assemble the desired construct(s). In certain embodiments the selection of initial materials, reaction steps, and synthesis protocol to assemble the desired biological construct is designed using the methods and/or software described in patent application no. 61/438,601, filed on Feb. 1, 2011, now U.S. Ser. No. 13/364,285, filed on Feb. 1, 2012, which are incorporated herein by reference for the software, methods and computer implemented inventions described therein) to design the combinatorial DNA assembly process.

In certain embodiments a method of assembling a biological construct is provided where the method comprises encapsulating separate components (e.g., genes, vectors, cells, etc.) of the biological construct each in a fluid droplet confined in a fluid channel; optionally mixing droplets from different fluid channels to form a sequenced order of droplets carrying different components of the biological construct in a channel or chamber; and optionally combining two or more droplets each containing different components of the biological construct to permit said components to react with each other in one or more reactions contributing to the assembly of said biological construct. In certain embodiments the two or more components comprise two or more components independently selected from the group consisting of a promoter, a terminator, a secretion signal, a gene, a vector, and a cell. In certain embodiments different droplets contain different genes. In certain embodiments two or more components react to ligate two or more genes together. In certain embodiments two or more components are subject to a restriction digest before or after ligation. In certain embodiments two or more components react to ligate a plurality of genes together under control of a promoter. In certain embodiments two or more components react to introduce said components into a vector. In certain embodiments the vector is a plasmid or cosmid. In certain embodiments the two or more components react in a self-assembling nucleic acid assembly system. In certain embodiments the assembly system comprises a system selected from the group consisting of BIOBRICK®, sequence and ligation independent cloning (SLIC), GIBSON®, circular polymerase extension cloning (CPEC), and GOLDEN-GATE®. In certain embodiments the two or more components react to introduce a nucleic acid construct and/or to express a contract in in a cell free modality. In certain embodiments the two or more components react to introduce a nucleic acid construct into a cell. In certain embodiments the cell is selected from the group consisting of a bacterial cell, a mammalian cell, an insect cell, a plant cell, an algal cell, and a fungal cell. In certain embodiments the method comprises identifying and optionally capturing/trapping transformed cells. In certain embodiments the droplets carry reagents sufficient to enable one or more procedures selected from the group consisting of amplification, cloning, expression, and cell transformation. In certain embodiments the fluid channels are in a microfluidics device. In certain embodiments the reactions are performed in a microfluidics device. In certain embodiments the nature and sequence of operations, droplet components, and/or reagent composition of droplets or reaction mixtures is determined and optionally under the control of instructions and/or software implementing instructions according to a j5 assembly protocol.

In various embodiments a microfluidic device for the assembly of a biological construct is provided. The microfluidic device typically comprises a configuration of microchannels and/or chambers, and/or ports to generate fluid droplets in a fluid channel and/or a fluid chamber; a configuration of microchannels and/or chambers or ports to introduce biological materials into said droplets; and optionally, a configuration of microchannels, and/or chamber, and/or ports, and/or valves to control and determine an order of droplets carrying different biological materials; and optionally, a configuration of microchannels, and/or chamber, and/or ports, and/or valves to control the combination and reaction of droplets carrying different biological materials and/or to control the reaction of said biological materials with each other. In certain embodiments the device is configured to merge droplets by electrocoalescence. In certain embodiments the device comprises one or more serpentine channels that direct droplets over a plurality of heating pads at different temperatures. In certain embodiments passage of droplets through the serpentine channel effects a polymerase chain reaction (PCR) within the droplet(s). In certain embodiments the serpentine channel(s) direct droplets over 4 heating pads each heating pad at a different temperature. In certain embodiments the device comprises microchambers configured to contain cells and to receive a flow of cell culture media. In certain embodiments the device is disposed under a microscope to permit visualization of cells in said device. In certain embodiments the device comprises a plurality of electrodes for detecting cells or droplets and/or for controlling droplet combination and/or for controlling fluid flow. In certain embodiments the device is configured to receive instructions and/or to perform operations (e.g., nucleic acid assembly operations, and/or cell transformation, and/or cell culture) as described herein. In certain embodiments the device is configured to receive instructions or software implementing instructions and/or to perform operations according to a j5 assembly protocol.

DEFINITIONS

The terms "microfluidic channel" or "microchannel" are used interchangeably and refer to a channel having at least one characteristic dimension (e.g., width or diameter) less than 1,000 µm, more preferably less than about 900 µm, or less than about 800 µm, or less than about 700 µm, or less than about 600 µm, or less than about 500 µm, or less than about 400 µm, or less than about 300 µm, or less than about 250 µm, or less than about 200 µm, or less than about 150 µm, or less than about 100 µm, or less than about 75 µm, or less than about 50 µm, or less than about 40 µm, or less than about 30 µm, or less than about 20 µm.

The term "immiscible" when used with respect to two fluids indicates that the fluids when mixed in some proportion, do not form a solution. Classic immiscible materials are water and oil. Immiscible fluids, as used herein also include fluids that substantially do not form a solution when combined in some proportion. Commonly the materials are substantially immiscible when they do not form a solution if combined in equal proportions.

When describing assembly strategies/methods the term "parts" simply refers to generalized DNA sequences.

DETAILED DESCRIPTION

Synthetic biology applications involve assembly of a plurality of biological parts (e.g., genes) in a plasmid, cosmid, or other similar construct. In certain instances, this can lead to a large combinatorial problem where several thousands of combinations of parts have to be assembled to product a particular biological construct. The scale of the problem is a significant challenge in terms of cost and time required to generate all the possible combinations.

We developed a software control and microfluidic platform that can overcome the throughout limitation of combinatorial biological parts assembly process. In addition, the integrated microfluidic platform can integrate screening of transformants based on their phenotype.

Figure 1:
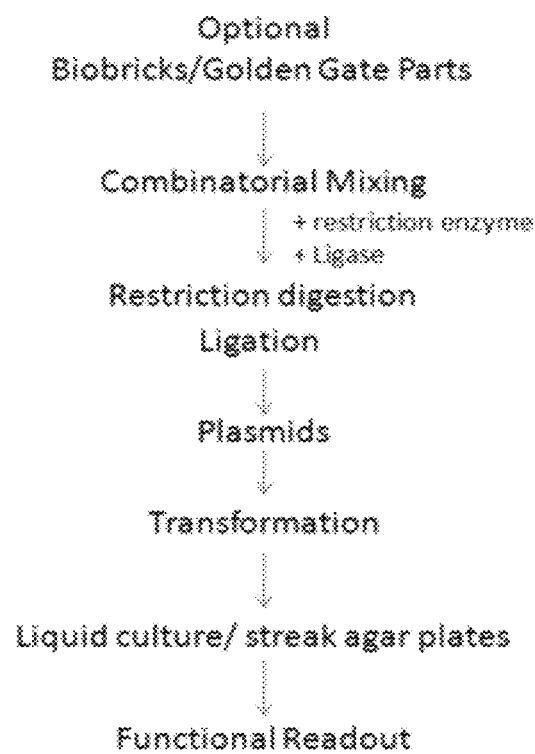
FIG. 1 schematically illustrates one process for synthesis of a biological construct.

An illustrative, but non-limiting flow chart showing steps in one sequence for combinatorial DNA assembly is shown in FIG. 1. The integration of some of these steps, all of these steps, and/or other steps has heretofore presented a major challenge. The methods and devices provided therein provide an effective solution to the rapid and effective integration of the steps utilized in synthetic biology, (e.g., the constructions of synthetic organisms and/or components thereof). In various embodiments the methods and devices described herein contemplate a droplet microfluidics-based approach for performing the various operations involved in synthetic biology (e.g., cloning a gene/cDNA, transfecting a cell, selecting a transformant, etc.).

Figure 2A:
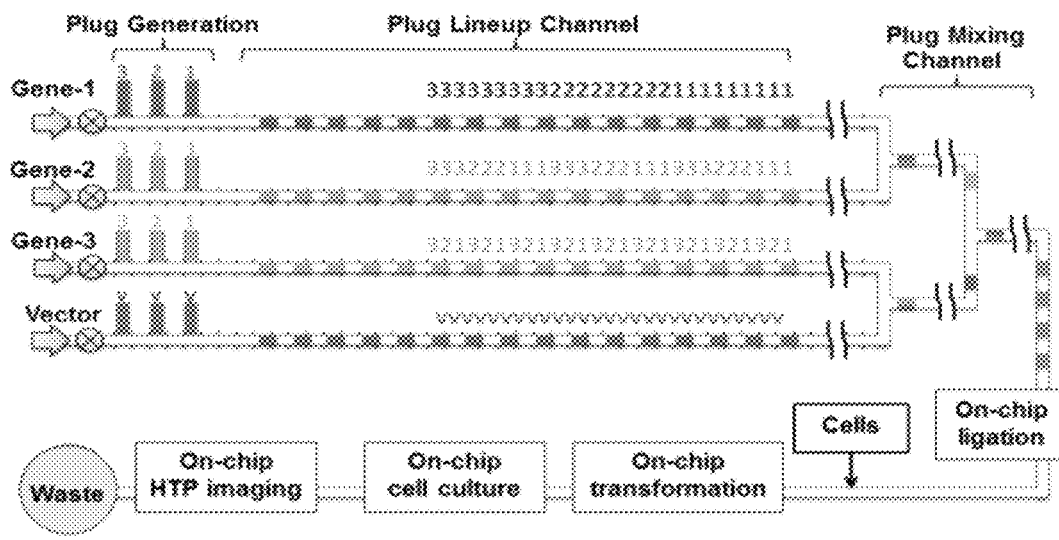
FIGS. 2A and 2B schematically illustrate exemplary droplet based microfluidic devices.
Figure 2B:
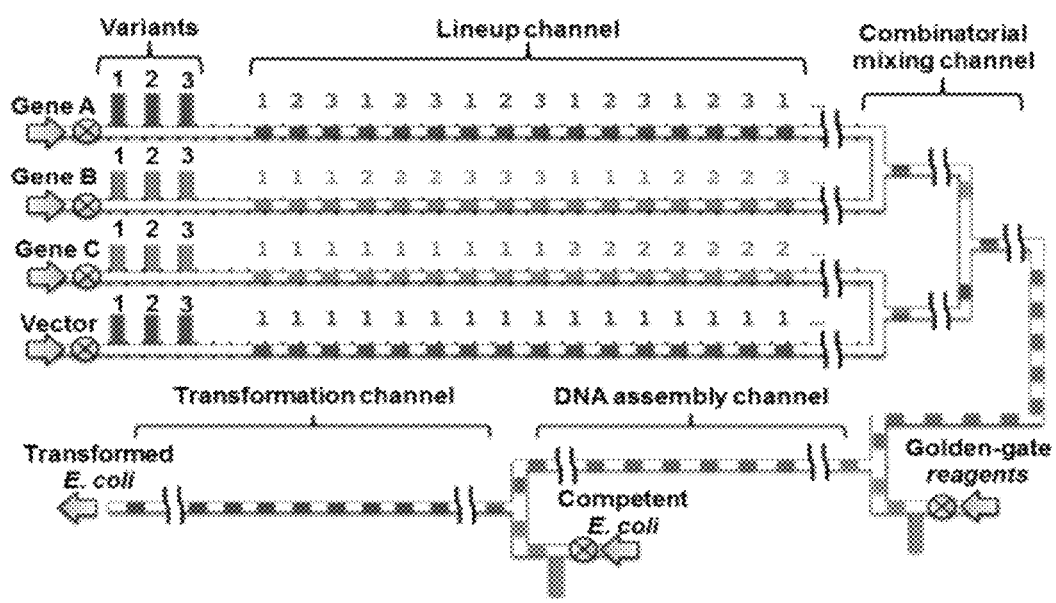

In various embodiments a droplet microfluidics-based approach is to overcome the large-scale combinatorial and screening problem (see, e.g., FIGS. 2A and 2B). The idea is to have genes (and/or other components of the desired biological construct) encapsulated in discrete droplets. Then combination of genes (or other components and/or reagents) can be produced by programmable merging of droplets. The droplets can carry reagents necessary to enable various cloning, expression, and transformation steps. Furthermore, the droplets maintain their discrete nature even when flow is stopped allowing one to carry out timed incubations and other steps. The entire chip can be operated at a temperature in the range of about 4° C. to about 95° C. enabling molecular biology reactions requiring, e.g., 4° C., 37° C. or any other temperature in the specified range.

In certain embodiments the mixing steps can involve mixing plasmids with cells so that the cells take up the plasmids (a process also referred to as transformation). Alternately or additionally, the plasmids can be mixed with a cell-free expression reagent to express protein in vitro. In various embodiments the droplets can carry cell culture media permitting growth and division of cells.

Figure 3:
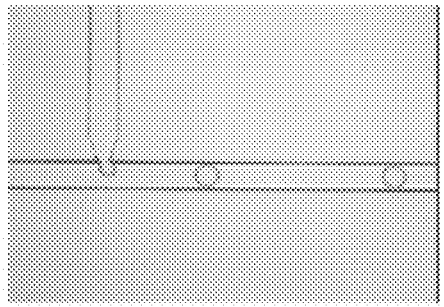
FIG. 3 illustrates formation of droplets in a microfluidic channel.
Figure 3:
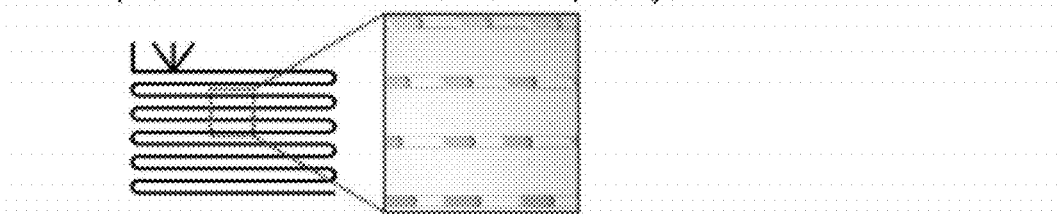

As illustrated in FIGS. 2A and 2B), biological components (e.g., genes, plasmids, etc.) can be encapsulated in droplets. In various embodiments the droplets are provided as a two-phase system (e.g., air/oil/water/organic solvent). In various embodiments the droplet is formed from a first fluid that is substantially immiscible in a second fluid. As illustrated in FIG. 3, the droplets can be formed by simply injecting one fluid through a channel or port into a channel, port, or chamber containing the second non-miscible fluid. In various embodiments the biological component(s) can be provided in the first fluid, or can be introduced at the time of droplet formation through a third port, or channel.

Figure 4:
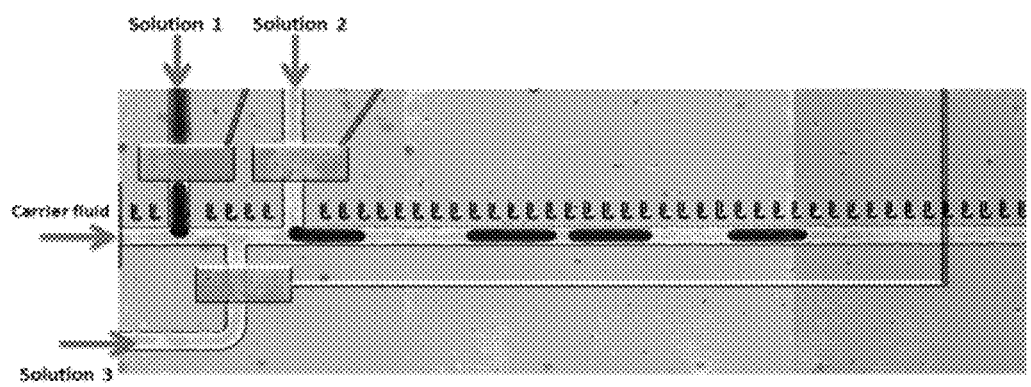
FIG. 4 illustrates droplet generation and queing.

Within the droplet-based microfluidic device (please see FIGS. 2A and 2B) for an approximate representative topological schematic); note that this invention is agnostic to the exact specifications of the microfluidic device; the number of assembly piece channels and the number of variants per assembly piece channel can easily exceed those illustrated), a series of line-up channels followed by combinatorial mixing channels generate a sequence of droplets containing the desired (but not necessarily exhaustive) combinatorial mixtures of DNA input parts or other components (see, e.g., FIG. 4). On-chip valves can be used to control the precise ordering of droplets.

Figure 5:
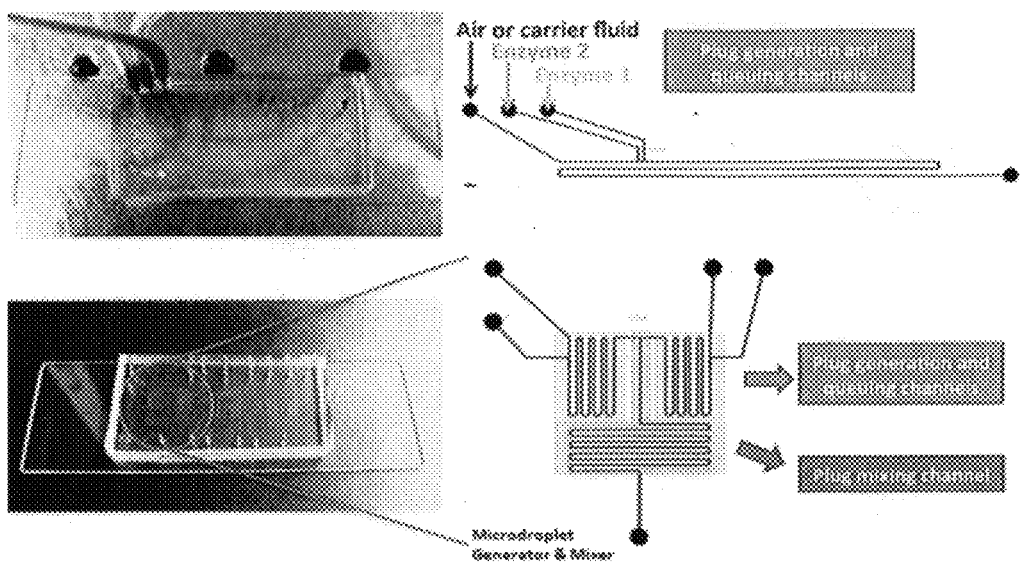
FIG. 5 shows illustrative, but not limiting, device designs.

Assembly reaction reagents (e.g., BIOBRICK®, sequence and ligation independent cloning (SLIC), GIBSON®, circular polymerase extension cloning (CPEC) Golden-Gate, etc.) can be mixed with these combinatorial mixture drop-lets, and the assembly reactions would proceed on-chip (see, illustrative device designs in FIG. 5). In certain embodiments subsequent to the completion of the assembly reactions, the droplets can be mixed with cells (e.g., competent *E. coli* cells, other bacterial cells, insect cells, mammalian (e.g., human) cells, plant cells, algal cells, fungal cells, etc.) and the transformation (e.g. heat-shock or chemically induced transfection) of the cells proceeds. In certain embodiments the transformed cells can then be cultured on the chip followed by phenotype screening (e.g., based on optical imaging). Of course, in certain embodiments, such cell transfection is not performed.

In certain embodiments, where cells are transfected/transformed, post transfection/transformation, the droplets could be diluted with cell culture media and then deposited into culture plates (e.g., 96-well plates) for out-growth and the subsequent processes required for liquid-culture monoclonal isolation (putatively but not necessarily with the assistance of a liquid-handling robotic platform). Alternatively, the droplets could be diluted with cell culture media, the transformed cells could be propagated on-chip for one or more cell-cycle(s) (e.g., approximately one hour), a selective agent (e.g. and antibiotic) could then be added to the drop-lets, the cells further propagated on-chip under selective pressure for multiple cell-cycles (e.g., approximately 12 hours), and optical cell-sorting could then generate one or more sub-droplets containing one-cell each (monoclonal isolation) per drop-let, and these monoclonal droplets could then be diluted with selective cell culture media and then deposited into cell culture plates (e.g., 96-well plates) for out-growth.

The microfluidic chip can easily be interfaced with an optical detection or imaging instrument (such as an optical microscope) to image cells, count them, or monitor expression of a fluorescent protein. In certain embodiments a fluorescence detector can be used to monitor cells, one-at-a-time, using flow cytometry integrated within the chip. The device also permits droplets to be taken out of the chip at any of the steps (e.g., any of the steps outlined in FIG. 1) for processing outside the chip. Examples include, but are not limited to PCR of products in a droplet or culturing of transformed cells in the droplets.

Figure 6:
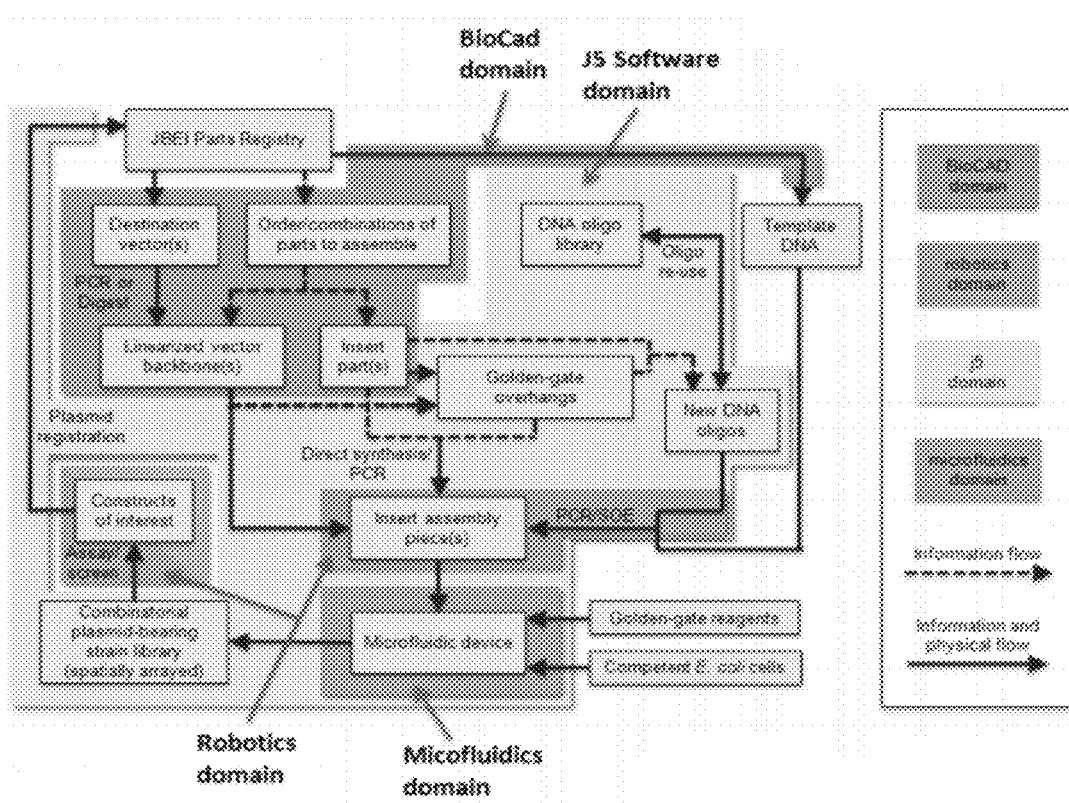
FIG. 6 schematically illustrates one process for synthesis of a biological construct.

The overall workflow of an illustrative process is shown in FIG. 6. The end-user can select DNA parts from sequence files and/or a database (e.g. the JBEI Parts Registry) as well as choose the order and the combinations of parts to assemble with biological computer-aided design (BioCAD) tool(s) (such as DeviceEditor, see its software disclosure documentation for more information), and then, optionally use j5 software as described in patent application no. 61/438, 601, filed on 1 Feb. 2011 and titled SCAR-LESS MULTI-PART DNA ASSEMBLY DESIGN AUTOMATION, now U.S. Ser. No. 13/364,285, filed on Feb. 1, 2012, which are incorporated herein by reference for the software, methods and computer implemented inventions described therein) to design the DNA assembly process. Following the assembly design process the user would provide appropriate materials (e.g., purchase the DNA oligos and direct DNA synthesis services required for the assembly), and perform the requisite digests and/or PCR reactions (putatively but not necessarily with the assistance of a liquid-handling robotic platform). Thereafter, appropriate vessels containing the resulting DNA parts to assemble (arrayed as directed for example, by the j5 software-derived assembly instructions), along with reservoirs of Golden-gate, or other, assembly reagents and cells (e.g., competent *E. coli* cells), would be connected to the microfluidic device. In certain embodiments these initial materials could be provided as output channels from robotic synthesizers and/or materials handlers, and/or other microfluidic systems.

In various embodiments typical materials inputs to the microfluidic device can include DNA, host cells, and reagents for assembly, amplification, transformation, lysis, and the like. Output from the device can be cultured transformed cells or any of the intermediate products including various vectors such as plasmids, cosmids, and the like.

In various embodiments the microfluidic device is a modular unit with multiple modes available to carry out mixing, reaction, and cell culture. In one configuration, it will also include an integrated cell sorter to impart the ability to select cells based one or more desired criteria. In various embodiments the microfluidic device can be compatible with many on- or off-chip detection techniques including electrochemical, conductivity and optical detection techniques such as absorbance, fluorescence, and light scattering. In various embodiments the device can also permit imaging of cells. The integrated detection/imaging permits monitoring of processes at every step in the microfluidic device facilitating trouble shooting and condition optimization. Conventional methods of DNA assembly and transformation do not allow this.

Figure 38:
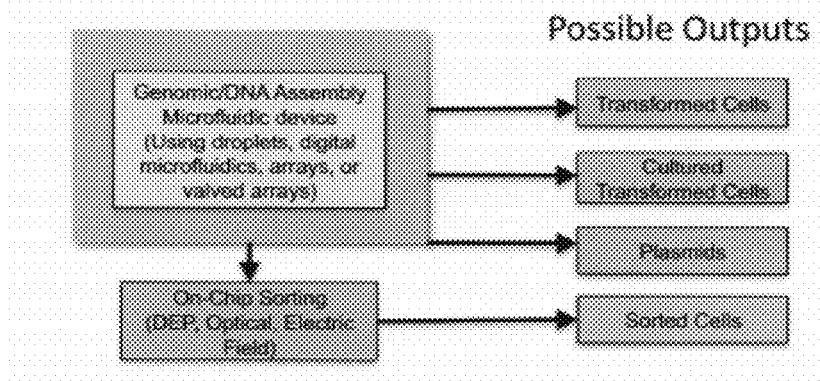
FIG. 38 shows illustrative, but not limiting possible outputs and device architectures (e.g., droplet-based, digital microfluidics, or array-based) of the microfluidic device. d

Illustrative, but not limiting possible outputs and device architectures (e.g., droplet-based, digital microfluidics, or array-based) of the microfluidic device are depicted in FIG. 38.

There are multiple productivity and efficiency benefits that end-users would derive from the methods and devices described herein. First, the microfluidic platform(s) described allow for the use of substantially smaller quantities of reagents/input DNA parts. Since multi-channel pipettes and liquid handling robotics platforms have minimum reliable transfer volumes (e.g. 5 micro-liters), large multi-part combinatorial libraries with thousands of constructs require significant amounts of assembly reagents, DNA parts to be assembled, and competent cells to be transformed. Second, the methods, systems, and devices provide dramatic advantages over that currently achievable with mixed one-pot combinatorial libraries, in that there would be no sequencing/PCR identification required (since the identity of each construct is known), each and every experiment would provide new information, and the need for over-sampling would be eliminated (although multiple clones of the same construct could still be assayed in replicate, if desired, to hedge against assembly defects). Third, the eliminated need for sequencing screen "hits" for identification purposes, and the reduced screening size burden, would jointly make enormous contributions towards time and cost savings over currently achievable methodologies. Furthermore, when combined with an in-line microfluidic screen/assay functionality, it is possible to dispense with the need for extremely capital-expensive liquid-handling robotics platforms (although they could still play a useful role in automating the steps required to generate the DNA assembly pieces that are input into the microfluidic device), and provide technological access to smaller/less well funded laboratories.

Droplet Fluids.

In certain embodiments the methods and devices described above use an oil/water system or an air/aqueous fluid system for droplet generation. However, the systems need not be so limited. For example, in certain embodiments, it is contemplated that any of a number of immiscible fluid systems can be used. Thus, for example, where the droplets are to be formed comprising an aqueous solvent (e.g., water), any of a number of immiscible fluids such as carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, 2,2,4-trimethylpentan, and the like are contemplated.

In certain embodiments the first fluid and second fluid need not be immiscible in each other. In such embodiments, injected droplets can be kept separate from each other simply by adjusting flow rates in the microchannels and rate of droplet formation to form separated droplets.

Microfluidic Device Operation

Operation, and Flow Control.

In certain illustrative embodiments sample solutions (e.g., buffer solutions, cell culture solutions, etc. (and carrier fluid (e.g., mineral oil with surfactant) are injected into the PDMS channels via ports and/or tubings and are driven by compressed air. The flow rates of solutions and oils can be controlled by pressure regulators.

In certain embodiments the droplets are formed by shearing force at the T-junction of the microchannel where oils and solutions meet. Droplet size, spacing, and transportation speed can be adjusted by fine tuning the ratio between solution and oil flow rate.

By opening different solution valves at different time, various droplet sequence can be generated and queue in the flow channel. Before two trains of droplets are mixed, a synchronization structure is utilized to ensure droplets arrive at mixing spot at the same time.

This approach is intended to be illustrative and not limiting. Any of a number of approaches can be used to convey the fluids, or mixtures of droplets, particles, cells, etc. along the channels of the devices described herein. Such approaches include, but are not limited to syringe pumps, peristaltic pumps, electrokinetic pumps, bubble pumps, air pressure driven pumps, and gravity-driven pumps.

Capacitive Detection of Droplets in Microfluidic Channel:

In certain embodiments the presence, size and speed of droplets in microfluidic channel can be detected by using commercially available capacitive sensors which make the droplet-based microfluidic systems scalable and inexpensive. Cross-contamination between the droplets can be eliminated by introducing a passivation layer between the sensing electrodes and droplets. Coplanar electrodes can be used to form a capacitance through the microfluidic channel. The change in capacitance due to the presence of a droplet in the sensing area can be detected and used to determine the size and speed of the droplet. A single pair of electrodes can be used to detect the presence of a droplet and the interdigital finger design can be used to detect the size and speed of the droplet. The measured droplet information can be displayed through a LABVIEW® interface in real-time.

Imaging Data Collection and Analysis:

In certain embodiments chambers in the microfluidic device have fresh nutrients flowing through for an incubation period, during which the cell growth and signal (usually fluorescence) can be monitored. An automated stage mounted to a microscope with a CCD camera can be used to rapidly collect and analyze each chamber. Stage operation can be operated via LABVIEW®, with image data analysis done with MATLAB®.

Assembly System Used in the Microfluidic (SynBioChip) Device.

In various embodiments the assembly techniques utilized in the devices described herein can employ standardized restriction enzyme assembly protocols. Such protocols include, but are not limited to BIOBRICKS®, BGL-BRICKS®, and Golden-Gate methods. In certain embodiments sequence-independent overlap techniques, such as IN-FUSION®, sequence and ligation independent cloning (SLIC), and GIBSON® isothermal assembly can be used for larger assemblies. In certain embodiments the device(s) described herein are configured to receive instructions or to receive software implementing instructions and/or to perform operations according to one or more assembly systems (e.g., gene assembly systems) described herein.

Such assembly systems/techniques are described below and using the teachings provided herein these and other assembly methods can readily be adapted for use in the systems and methods described herein.

Multiple Cloning Site Approach

One illustrative DNA assembly technique readily implemented in the devices described herein is the multiple cloning site, restriction enzyme, ligase cloning approach. Typically an expression vector is provided that comprises a multiple cloning site (MCS) following a promoter (e.g., a T7 promoter). The MCS is in turn followed by a terminator (e.g., a T7 terminator). If a protein coding sequence is to be integrated into the expression vector two restriction sites present in the MCS, but absent in the coding sequence of interest are identified. The coding sequence of interest can be PCR amplified using DNA primers flanked with the selected restriction sites. The PCR product as well as the destination vector is digested with the corresponding restriction enzymes. The Digested PCR product and destination vector backbone are purified (e.g., gel-purified), and the purified digested PCR product and destination vector are ligated thereby inserting the coding sequence into the destination vector. The resulting construct can then be transfected into target host cells (e.g., competent *E. coli*).

This approach works well for integrating a single coding sequence into the MCS of the destination expression vector. The large number of multiple cloning sites (e.g., 11 or more in certain vectors) results in a high likelihood that at least two of the sites will be absent from the coding sequence of interest. However, when incorporating multiple DNA sequence fragments into the same destination vector, such as an entire metabolic pathway or genetic circuit, it becomes more difficult to identify restriction sites that don't occur in the sequences that are to be cloned into the vector.

The problem of restriction sites occurring in the sequences that are to be introduced into the target vector has been addressed with various strategies. A non-exhaustive set of examples includes: adding (silent) point mutations to DNA fragments to disrupt restriction site sequences, splicing together two or more fragments with PCR (e.g. splicing by overlap extension (SOE)), using compatible single-stranded overhangs that (when ligated) do not result in a recognizable/recleavable restriction site, partial DNA digests, annealing single stranded DNA fragments to yield double stranded DNA with the desired single stranded overhangs, site specifically protecting a methyl-sensitive restriction enzyme site from methylation with a DNA oligo/RecA complex, sequentially performing the assembly hierarchically (so that the same restriction site may potentially be used more than once, and so forth. It is noted that direct DNA synthesis, while perhaps cost-prohibitive at the moment (although certainly less so in the near future), is a very viable alternative to DNA assembly in general, and has the capacity to make many of these obstacles and concerns obsolete. We will return to direct DNA synthesis during the brief survey of j5 functionality.

The BIOBRICK®, sequence and ligation independent cloning (SLIC), GIBSON®, circular polymerase extension cloning (CPEC), and Golden-Gate DNA assembly methods utilize, or are derived from, many of these modifications to the multiple cloning site method and are also readily implemented in the methods and devices described herein. What sets these methods apart from the traditional approach is "standardization". In traditional cloning, the set of selected restriction enzymes (as well as the point mutations made to disrupt undesired replicate restriction sites) is entirely dependent on the number, sequences and order of the fragments to be assembled. Thus, every different assembly might require a different combination of restriction enzymes, point mutations, reaction temperature and buffer conditions. Furthermore, a given sequence fragment may have to be re-cloned entirely for each new assembly, precluding re-use. While restriction enzyme companies (such as NEB and Fermentas), have made much progress in ensuring that all of their restriction enzymes can operate under a single reaction condition (temperature, buffer, etc.), in general, it is very unlikely that a single enzymatic "master mix" can be applied across independent traditional assemblies, making the process less amenable to parallelization and automation (especially via high-throughput liquid handling robotics platforms).

The BIOBRICK®, SLIC/GIBSON®/CPEC and GOLDEN Golden-Gate methods, in contrast, use the same (standardized) set of enzymes and reaction conditions for every assembly. When point mutations are required (as is potentially the case for BioBrick and Golden-gate assembly, which utilize restriction enzyme(s)), the same mutations are required for every assembly, and thereby each sequence fragment only needs to be cloned once, facilitating re-use. Thus, these standardized methods are much more amenable to parallelization and automation than the traditional approach.

BioBrick Approach

The BIOBRICK® approach standardizes the DNA assembly process, and facilitates automation and part re-use. There are several BIOBRICK® assembly standards, such as that originally developed at MIT (see, e.g., Shetty et al. (2008) *J. Biol. Eng.*, 2: 5), as well as the UC Berkeley BglBrick standard (see, e.g., Anderson et al. (2010) *J. Biol. Eng.*, 4: 1).

In the BGLBRICK® standard, a part (or DNA sequence fragment that is nominally associated with a biological function) is flanked with two restriction enzyme sites at its 5' end, namely EcoRI and BglII, and is flanked with BamHI and XhoI at its 3' terminus. To comply with the BGL-BRICK® standard, these four restriction sites must be absent from the sequence of the part itself. The "BglBrick", then, spans from the EcoRI to the XhoI site, and the BGLBRICK®-bearing vector backbone makes up the residual plasmid sequence, which should also be devoid of the four BGLBRICK® restriction sites. To assemble partA followed by partB, followed by the partA-bearing vector backbone, the partA BGLBRICK® vector is digested with BamHI and XhoI, and the partB vector is digested with BglII and XhoI. The resulting digest fragments containing partA and partB are then ligated together, resulting in the desired plasmid. The overhang sequences resulting from BamHI and BglII digest are complementary (base-pair/anneal perfectly with one-another), but the resulting ligation product sequence is not recognized/recleaved by either BamHI or BglII. Thus, the assembly results in a new BGLBRICK®, containing partA followed by a six bp scar sequence, followed by partB. A key consequence of BglBrick assembly is that assembling two parts results in a new BGLBRICK®, so that this process can be iterated successively to assemble an arbitrary number of parts together, using the same protocol repetitively. It is possible to assemble partB in front of partA, and/or to select the partA or partB-bearing vector backbone for the resulting construct, by using different combinations of the four BGLBRICK® restriction enzymes. Other BGLBRICK® standards are completely analogous to BGLBRICKS®, and simply use alternate sets of the four restriction enzymes.

Contrasting with the traditional approach, there are several advantages to using BGLBRICKS®: 1) only four restriction enzymes are utilized, 2) once a part is BioBrick'd, it is never necessary to re-clone it (or even re-PCR amplify it, reducing the probability of PCR-derived mutations), and 3) assembling an arbitrary number of parts (in any desired arrangement) is no more difficult than putting two together (plasmid size considerations aside). In contrast with SLIC, GIBSON®, CPEC, and Golden-Gate methods, BIO-BRICK® assembly not only standardizes the assembly process (e.g. the set of four restriction enzymes, protocols, etc.), but also physically standardizes the BioBrick'd parts themselves, as they all have the same 5' and 3' terminal sequences, and internally share the same 6-bp scar vestiges of prior assemblies. There are burgeoning repositories of these standardized parts (physical and/or informatic), such as the MIT Registry of Standard Biological Parts, and supporting organizations, such as the BIOBRICKS® Foundation, that allow and facilitate researcher re-use of characterized and validated parts, preempting wasteful redundant efforts.

FIG. 1D in application no. 61/438,601, filed on 1 Feb. 2011, now U.S. Ser. No. 13/364,285, filed on Feb. 1, 2012, which are incorporated herein by reference, depicts how the prior art BIOBRICK® approach could be used to assemble a pathway. Note that there are many different possible routes (assembly trees) to put together this pathway using Bio-Bricks. Some of the intermediate parts, such as the terminator fused to the promoter, need only be made once, and can be re-used multiple times. Recently, algorithms have been developed (see, e.g., Densmore et al. (2010) *Nucl. Acids Res.* 38(8): 2607-2616) to optimize the design of binary BIOBRICK® assembly trees.

(SLIC), GIBSON®, and CPEC Assembly Methods

The SLIC, GIBSON®, and CPEC DNA assembly methods are related methods that offer standardized, scarless, (largely) sequence-independent, multi-part DNA assembly. Some discussion of the advantages of each method over the others is provided below.

SLIC, or sequence and ligase independent cloning (see, e.g., Li et al. (2007) *Nature Meth.,* 4: 251-256), as its name implies, does not utilize restriction enzymes or ligase. A DNA sequence fragment to be cloned into a destination vector is PCR amplified with oligos (oligonucleotides) whose 5' termini contain about 25 bp of sequence homology to the ends of the destination vector, linearized either by restriction digest or PCR amplification.

The linearized destination vector and the PCR product containing partA are separately treated with T4 DNA polymerase in the absence of dNTPs. In the absence of dNTPs, T4 DNA polymerase has 3' exonuclease activity, which begins to chew-back the linearized destination vector and the PCR product from 3' to 5'. Once the termini of the linearized destination vector and the PCR product have sufficient complementary single-stranded 5' overhangs exposed, dCTP is added to arrest the chew-back reaction. With the addition of dCTP, the T4 DNA polymerase changes activity from 3' exonuclease to polymerase, but stalls because not all dNTPs are present, retaining most, if not the entirety, of each chewed-back overhang. Alternatives to the 3' chew-back with T4 DNA polymerase in the absence of dNTPs include the use of mixed or incomplete PCR products (so this does not apply to the linearized vector backbone if it is derived from a restriction enzyme digest), which can also result in the desired 5' overhangs, as described in the original SLIC publication (Id.). The chewed-back linearized destination vector and PCR product are mixed together, and annealed to each other. Since there is no ligase in the reaction, this results in a plasmid with four single stranded gaps or nicks. Once transformed into competent *E. coli*, the gaps are repaired. SLIC assembly is standardized, in that it always uses the same reaction components and conditions, scar-less, since there is no sequence in the resulting assembly that is not user-designed, and sequence-independent, as the method is not (at least to a large extent) sensitive to the sequences of either the destination vector or the part to be incorporated.

GIBSON® DNA assembly, so named after the developer of the method (see, e.g., Gibson et al. (2009) *Nature Meth.,* 6: 343-345), is analogous to SLIC, except that it uses a dedicated exonuclease (no dNTP addition step), and uses a ligase to seal the single stranded nicks.

By way of example, (gene(s) of interest (partA) can be assembled with a linearized destination vector using the Gibson method. The linearized destination vector and the PCR product containing partA are mixed together with T5 exonuclease, which chews-back the linearized destination vector and the PCR product from 5' to 3, phusion polymerase, which (with the annealed linearized destination vector and PCR product effectively priming each other) fills in the gaps, and ligase, which seals the four single stranded nicks. The polymerase chases the exonuclease around the plasmid, with the polymerase eventually overtaking, as the exonuclease is gradually heat-inactivated (and Phusion is extremely fast). Like SLIC, GIBSON® assembly is standardized, scar-less, and largely sequence-independent. GIBSON® is advantageous over SLIC in that it is a simultaneous one pot reaction (the two-step addition of dCTP is not required), the presence of ligase may boost assembly efficiency, and since the assembly reaction occurs at an elevated temperature relative to SLIC, there may be fewer problems when somewhat stable secondary structures occur at the ends of assembly pieces; the disadvantage of the GIBSON® method is that the T5 exonuclease, Phusion polymerase, and Taq ligase cocktail is more expensive than that required for SLIC (only T4 DNA polymerase, or none at all if mixed or incomplete PCR products are used). An anecdotal/empirical limitation of the Gibson method is that it works best to assemble DNA fragments that are at least 250 bp in length or longer; this is perhaps due to the likelihood that the T5 exonuclease would entirely chew through a short DNA fragment before it has a chance to anneal and prime the Phusion polymerase for extension. While the same could be said for SLIC, the timing of dCTP addition provides some control in switching from the exonuclease to the polymerase activity of T4 DNA polymerase (the use of mixed or incomplete PCR products can prevent this problem all together), although caution should be applied when using SLIC to assemble small DNA fragments. Prior to GIBSON® (or SLIC) assembly, it is recommended to SOE (splice by overlap extension) together neighboring assembly fragments until their cumulative size is larger than 250 bp. Fortunately, the very same PCR products designed for GIBSON® (and SLIC) assembly, already contain the flanking homology sequences required for SOEing.

CPEC, or circular polymerase extension cloning (see, e.g., Quan and Tian (2009) *PLoS ONE* 4(7): e644), is analogous to SOEing together the fragments to be assembled, except that no oligos are utilized (the linearized destination vector and PCR product prime each other, as in SLIC®/GIBSON® assembly) and there are typically only a few thermo-cycles required.

Since there are no (or very few) re-amplifications of a given template sequence, PCR-derived mutations are not propagated to the same extent as one would anticipate for standard SOEing reactions. Like SLIC and GIBSON® assembly, CPEC is standardized, scar-less, and largely sequence-independent. CPEC is advantageous in that, since there is no exonuclease chew-back, small sequence fragments can be assembled directly without a preliminary SOEing step. There is no dNTP addition step (unlike SLIC), there is only a single enzyme (polymerase) required (unlike GIBSON®), and since the CPEC assembly reaction occurs at higher temperatures than either SLIC or GIBSON®, stable secondary structures at the ends of assembly pieces are relatively less of a concern.

Golden-Gate Assembly Method(s)

The Golden-Gate method (see, e.g., Engler et al. (2008) *PLoS ONE*, 3(11): e3647; Engler et al. (2009) *PLoS ONE* 4(5): e5553) offers standardized, quasi-scarless, multi-part DNA assembly, and is an excellent choice for combinatorial library construction. The Golden-Gate method relies upon the use of type IIs endonucleases, whose recognition sites are distal from their cut sites. Although there are several different type IIs endonucleases to choose from, one example uses BsaI (equivalent to Eco31I) (the GOLDEN-GATE® method only uses a single type IIs endonuclease at time).

In one illustrative implementation, the BsaI recognition sequence "GGTCTC" is separated from its four bp overhang by a single bp, and BsaI activity is independent of the sequences of the single bp spacer and the four bp overhang. The recognition site for BsaI is not palindromic, and is therefore directional. The PCR product containing partA in the example above is flanked by two BsaI recognition sites, both pointing inward towards partA, with a first overhang at its 5' terminus and a second overhang at its 3' end. If the PCR product shown above is mixed with BsaI and ligase, the PCR product is (reversibly) digested, resulting in three DNA fragments and ligated back together again. The same is true of the linearized destination vector. However, if the PCR product and the linearized destination vector (each of which contains one two overhangs) are both mixed together with BsaI and ligase, the cut linearized destination vector will irreversibly ligate (dead-end reaction product) with the cut PCR product containing partA. This particular ligation is irreversible, because the ligation product no longer contains any BsaI recognition sequences. Thus, over time, all reactions tend towards the desired assembly product. Golden-Gate assembly is scar-less, since we have complete control over the sequence of the resulting assembly product. There are some exceptions to this (such as the overhang sequences themselves must not be palindromic (or they would be self-complimentary), and any two overhang sequences must differ by at least one and preferably two bps so that the different overhangs are not cross-complimentary), but in general this is not an issue, because one can shift the relative overhang position and still end up with a scar-less assembly. The original Golden-Gate method calls for the assembly using uncut plasmids, in contrast with PCR products, and a PCR-linearized destination vector used in some protocols. The proposed benefit of using uncut plasmids as the source material is that it is easier to control the assembly stoichiometry, and with each of the plasmid substrates sequence verified and without the use of PCR, accumulating PCR-derived point mutations is not a concern. The limitation of using uncut plasmids as the source material is that the destination vector, and all of the parts to be assembled, must already be cloned into a Golden-gate format plasmid system, and the overhang sequences are set in stone. While PCR amplifying the destination vector backbone and the parts to assembly may result in PCR-derived point mutations, using PCR products as the Golden-Gate assembly source material provides the freedom to use any destination vector, and any parts to be assembled into it, without an initial round of cloning that locks in the overhang sequences. One additional point is that for optimal performance of Golden-Gate assembly, the linearized destination vector and the part to be incorporated should lack any additional BsaI recognition sites, other than those explicitly depicted in the example above. Since the digestion/ligation reaction is reversible for any internal BsaI recognition sites, it is generally not obligatory to make (silent) point mutations to remove them, however it is usually preferable to do so to maximize efficiency, and to assure that the internal overhang sequences will not anneal to the designed overhangs, and lead to incorrect assemblies.

Golden-Gate assembly is a particularly good choice for constructing combinatorial libraries. Every part in each combinatorial bin (the linearized destination vector is the first bin, the red, orange and yellow parts the second, and the purple, blue and green parts are the third) is flanked by the same two 4-bp overhang sequences.

j5 Assembly Methods.

In certain embodiments assembly methods include the assembly methods described in application no: 61/438,601, filed on 1 Feb. 2011 and titled SCAR-LESS MULTI-PART DNA ASSEMBLY DESIGN AUTOMATION, now U.S. Ser. No. 13/364,285, filed on Feb. 1, 2012 (which are incorporated herein by reference for the software, methods and computer implemented inventions described therein) are used to design the DNA assembly process.

In one exemplary embodiment described therein, the method(s) described therein include (1) receiving a list of DNA sequence fragments to be assembled together and an order in which to assemble the DNA sequence fragments, (2) determining a cost-minimizing assembly strategy for each of the DNA sequence fragments, (3) designing DNA oligonucleotides (oligos) in accordance with the cost-minimizing assembly strategy, (4) creating a plan for adding flanking homology sequences to each of the DNA oligos in accordance with the cost-minimizing assembly strategy, (5) checking the plan against oligo mis-priming and against assembly piece incompatibility events, and (6) outputting an experimental protocol and a DNA sequence file of the DNA assembly based on the checked plan.

In an exemplary embodiment described therein, the methods include (1) receiving a list of DNA sequence fragments to be assembled together and an order in which to assemble the DNA sequence fragments, (2) determining a cost-minimizing assembly strategy for each of the DNA sequence fragments, (3) designing direct synthesis pieces and DNA oligonucleotides (oligos) in accordance with the cost-minimizing assembly strategy, (4) creating a plan for adding flanking homology sequences to each of the direct synthesis pieces in accordance with the cost-minimizing assembly strategy, (5) checking the plan against oligo mis-priming and against assembly piece incompatibility events, and (6) outputting an experimental protocol and a DNA sequence file of the DNA assembly based on the checked plan.

In an exemplary embodiment described therein, the methods includes (1) receiving a list of DNA sequence fragments to be assembled together and an order in which to assemble the DNA sequence fragments, (2) determining a cost-minimizing assembly strategy for each of the DNA sequence fragments, (3) designing DNA oligonucleotides (oligos) and direct synthesis pieces in accordance with the cost-minimizing assembly strategy, (4) creating a plan for adding flanking homology sequences to each of the DNA oligos and to each of the direct synthesis pieces in accordance with the cost-minimizing assembly strategy, (5) checking the plan against oligo mis-priming and against assembly piece incompatibility events, and (6) outputting an experimental protocol and a DNA sequence file of the DNA assembly based on the checked plan.

In an exemplary embodiment described therein, the method includes (1) receiving a list of DNA sequence fragments to be assembled together and an order in which to assemble the DNA sequence fragments, (2) determining a cost-minimizing assembly strategy for each of the DNA sequence fragments, (3) designing DNA oligonucleotides (oligos) in accordance with the cost-minimizing assembly strategy, (4) creating a plan for adding optimized overhang sequences to each of the DNA oligos in accordance with the cost-minimizing assembly strategy, (5) checking the plan against oligo mis-priming, and (6) outputting an experimental protocol and a DNA sequence file of the DNA assembly based on the checked plan.

In an exemplary embodiment described therein, the method includes (1) receiving a list of DNA sequence fragments to be assembled together and an order in which to assemble the DNA sequence fragments, (2) determining a cost-minimizing assembly strategy for each of the DNA sequence fragments, (3) designing direct synthesis pieces and DNA oligonucleotides (oligos) in accordance with the cost-minimizing assembly strategy, (4) creating a plan for adding optimized overhang sequences to each of the direct synthesis pieces in accordance with the cost-minimizing assembly strategy, (5) checking the plan against oligo mis-priming, and (6) outputting an experimental protocol and a DNA sequence file of the DNA assembly based on the checked plan.

In an exemplary embodiment described therein, the method includes (1) receiving a list of DNA sequence fragments to be assembled together and an order in which to assemble the DNA sequence fragments, (2) determining a cost-minimizing assembly strategy for each of the DNA sequence fragments, (3) designing DNA oligonucleotides (oligos) and direct synthesis pieces in accordance with the cost-minimizing assembly strategy, (4) creating a plan for adding optimized overhang sequences to each of the DNA oligos and to each of the direct synthesis pieces in accordance with the cost-minimizing assembly strategy, (5) checking the plan against oligo mis-priming, and (6) outputting an experimental protocol and a DNA sequence file of the DNA assembly based on the checked plan.

Given (e.g., putatively combinatorial) sequences of a linearized vector backbone and insert parts, the methods described in U.S. Ser. No. 61/438,601 (now U.S. Ser. No. 13/364,285) design SLIC/GIBSON®/CPEC flanking homology sequences or Golden-Gate overhangs for each assembly piece, and perform an analysis to determine for which, if any, portions of the assembly direct synthesis would be more cost-effective than either PCR/SOE or oligo embedding. The methods then design the resulting DNA sequences for cost-effective direct synthesis, as well as the DNA oligos (suggesting re-use of existing oligos where possible) to amplify the desired assembly pieces. Finally, the methods output the PCR reactions to perform, details the resulting DNA sequences that will be assembled together, check for any incompatibilities between the assembly pieces, and prepare an annotated sequence file for the resulting assembly. Thus, the methods automate the tedious, laborious, and error-prone portions of the DNA assembly design process. Furthermore, the methods condense/aggregate multiple independent assembly designs (into 96-well plate format or other standard formats), including optimally distributing reactions across a thermo-cycler annealing temperature gradient, thereby facilitating the execution of assembly protocols utilizing liquid handling robotics. The methods are also easily integrated with the microfluidics devices described herein.

Flanking Homology Sequences

FIG. 6 depicts a process flow of an exemplary embodiment of the methods for designing assembly protocols using flanking homology sequences via SLIC/Gibson/CPEC assembly. In an illustrative embodiment, the methods allow for the selection of parts to assemble from a Registry of Biological Parts (e.g., the JBEI Parts Registry) or a local collection of DNA sequences. In various embodiments the methods can use BioCAD (biological computer-aided design) tools in this process. Specifically, to the benefit of SLIC/Gibson/CPEC BioBrick-compatible assembly, in an exemplary embodiment, the present methods use BioCAD tools (1) to suggest viable alternatives to undesirable repeated homologous sequences (e.g., identifying two distinct terminators with comparable function), and/or (2) to suggest point mutations to make that disrupt internal BioBrick/BsaI restriction sites, and/or (3) to query collections of DNA sequences for physically existing and available sequences that already contain two or more of the parts to be assembled together in the proper order and proper orientation, thereby reducing redundant fragment assembly steps where at all possible. The method then categorizes the parts to be assembled into either the linearized destination vector, or insert parts. The linearized destination vector can be nominally physically achieved by digesting the destination vector with restriction enzymes or by polymerase chain reaction (PCR)-amplifying the vector backbone, although direct DNA synthesis of an entire vector backbone could be done as well.

Given the sequences of the linearized vector backbone and the insert parts, the method designs the flanking homology sequences for each assembly piece, and performs an analysis to determine for which, if any, portions of the assembly direct synthesis would be more cost-effective than either PCR/SOE or oligo embedding. The present invention then designs DNA oligos for synthesis, and/or suggests re-use of existing oligos where possible, to amplify the desired assembly pieces. Notably, the vector backbone and/or any of the insert parts to be assembled do not necessarily need to physically exist (a prerequisite endonuclease digestion or PCR amplification) before the present invention is used to design the assembly, since it is possible to specify a direct synthesis strategy for any assembly fragment.

The method allows for liquid handling robotics or other devices to assist the execution of PCR/SOE to generate the assembly pieces, as well as their subsequent SLIC/GIBSON®/CPEC assembly. The method facilitates this process by condensing/aggregating designs for multiple independent assemblies (into 96-well plate format, including optimally distributing reactions across a thermo-cycler annealing temperature gradient. After transforming a competent cloning strain with the assembly reaction, the present invention sequence verifies a clonal isolate of the assembled plasmid, and deposits the clonal isolate into the parts registry or local collection for subsequent re-use.

DNA Oligonucleotides (Oligos)

Figure 7:
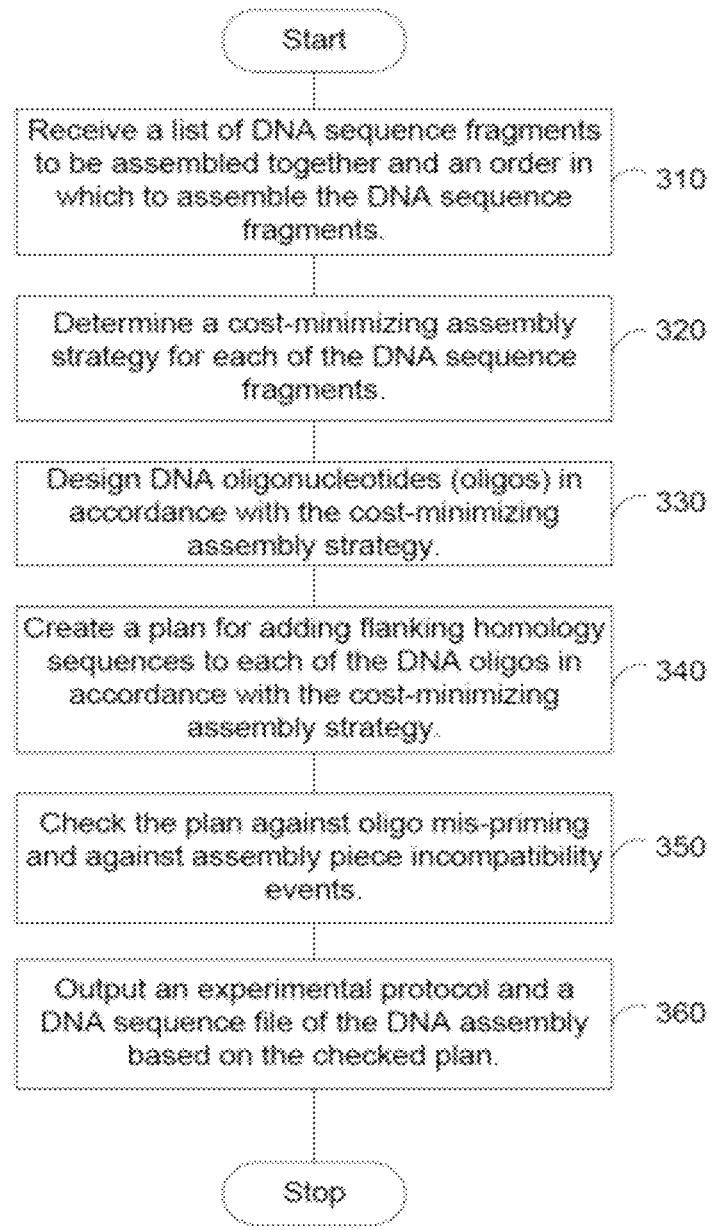
FIG. 7 illustrates one method used to design the DNA assembly process.

Referring to FIG. 7, in an exemplary embodiment, the method includes a step 310 of receiving a list of DNA sequence fragments to be assembled together and an order in which to assemble the DNA sequence fragments, a step 320 of determining a cost-minimizing assembly strategy for each of the DNA sequence fragments, a step 330 of designing DNA oligonucleotides (oligos) in accordance with the cost-minimizing assembly strategy, a step 340 of creating a plan for adding flanking homology sequences to each of the DNA oligos in accordance with the cost-minimizing assembly strategy, a step 350 of checking the plan against oligo mis-priming and against assembly piece incompatibility events, and a step 360 of outputting an experimental protocol and a DNA sequence file of the DNA assembly based on the checked plan.

Receiving

Figure 8A:
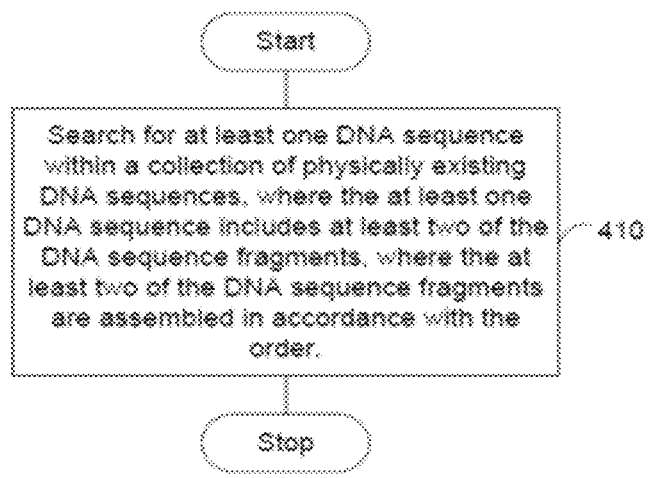
FIGS. 8A-8E illustrate various components of one method used to design the DNA assembly process.
Figure 8B:
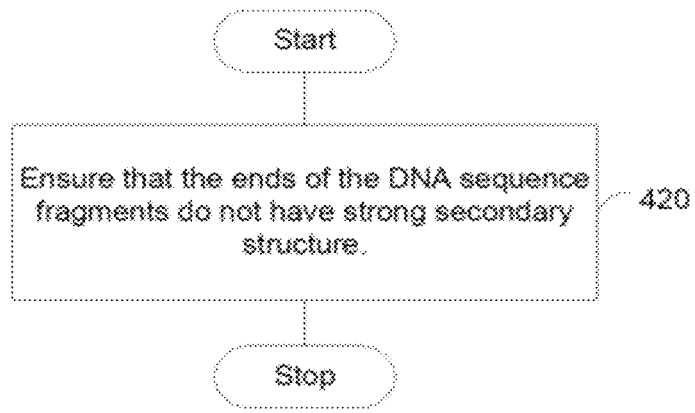

Referring to FIG. 8A, in an exemplary embodiment, receiving step 310 further includes a step 410 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 8B, in an exemplary embodiment, receiving step 310 further includes a step 420 of ensuring that the ends of the DNA sequence fragments do not have strong secondary structure.

Figure 8C:
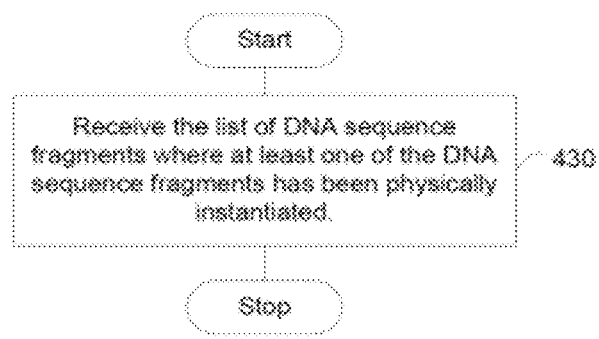
Figure 8D:
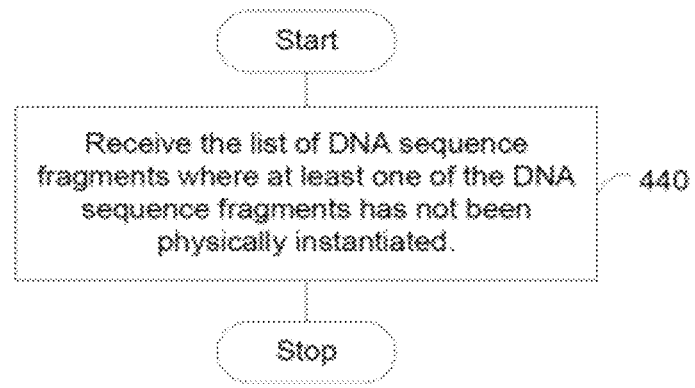
Figure 8E:
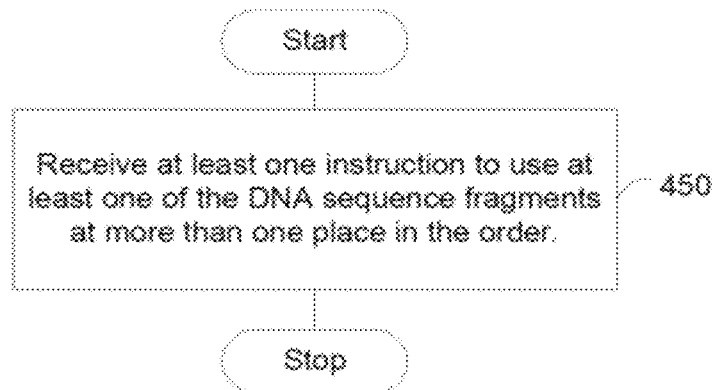

Referring to FIG. 8C, in an exemplary embodiment, receiving step 310 includes a step 430 of receiving the list of DNA sequence fragments where at least one of the DNA sequence fragments has been physically instantiated. Referring to FIG. 8D, in an exemplary embodiment, receiving step 310 includes a step 440 of receiving the list of DNA sequence fragments where at least one of the DNA sequence fragments has not been physically instantiated. Referring to FIG. 8E, in an exemplary embodiment, receiving step 310 includes a step 450 of receiving at least one instruction to use at least one of the DNA sequence fragments at more than one place in the order.

Creating

Figure 9A:
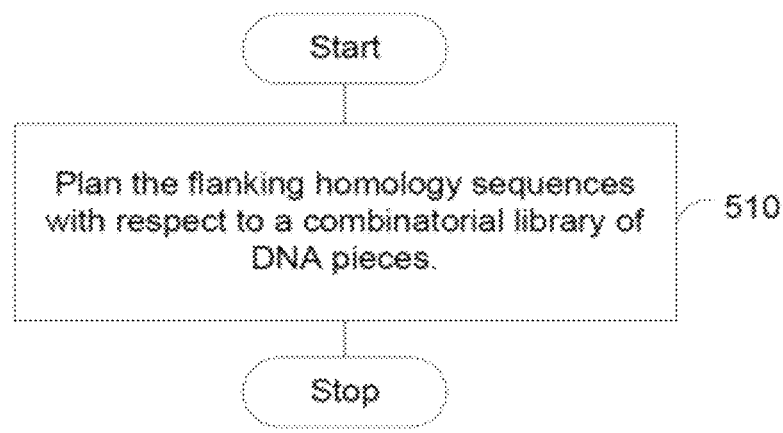
FIGS. 9A and 9B illustrate various components of one method used to design the DNA assembly process.
Figure 9B:
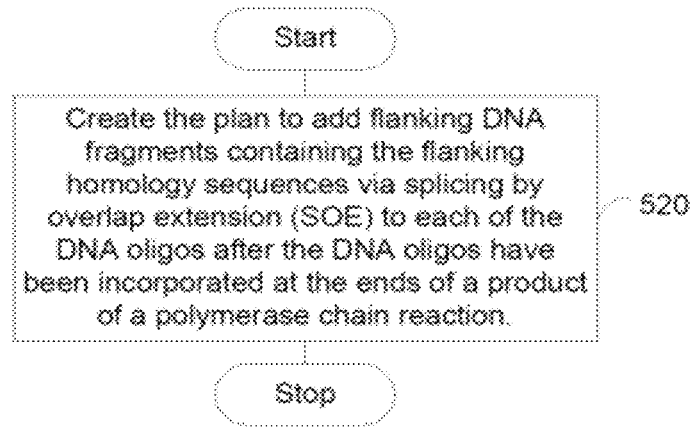

Referring to FIG. 9A, in an exemplary embodiment, creating step 340 includes a step 510 of planning the flanking homology sequences with respect to a combinatorial library of DNA pieces. Referring to FIG. 9B, in an exemplary embodiment, creating step 340 includes a step 520 of creating the plan to add flanking DNA fragments containing the flanking homology sequences via splicing by overlap extension (SOE) to each of the DNA oligos after the DNA oligos have been incorporated at the ends of a product of a polymerase chain reaction.

Checking

Figure 10A:
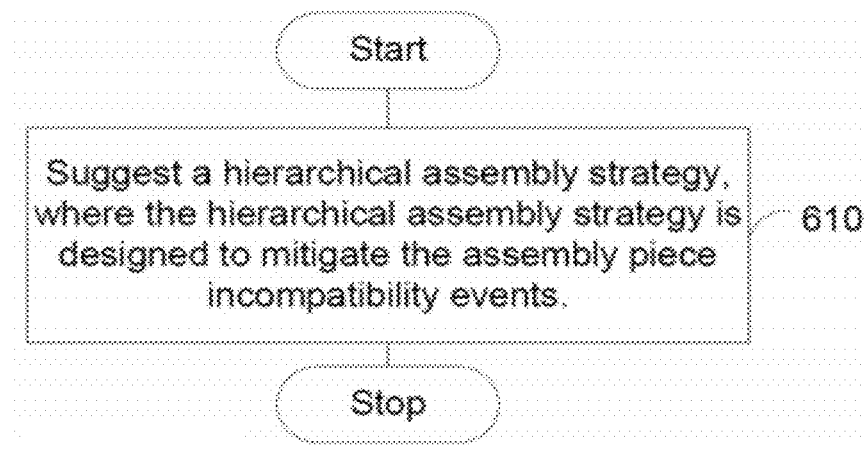
FIGS. 10A and 10B illustrate various components of one method used to design the DNA assembly process.
Figure 10B:
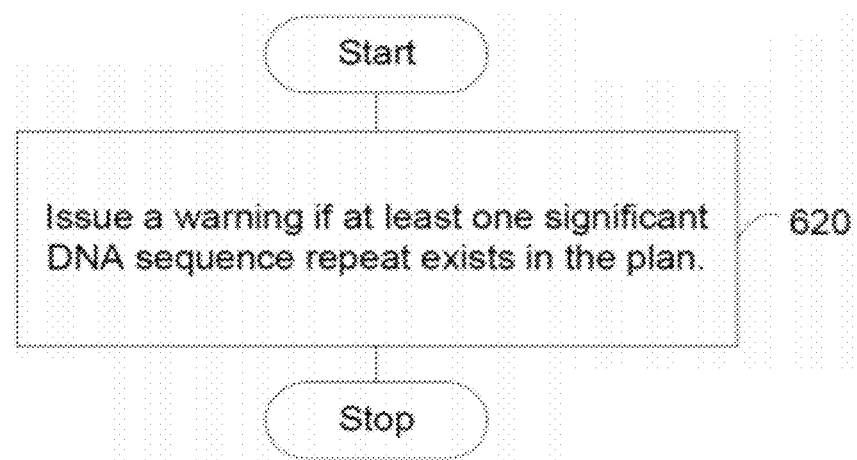

Referring to FIG. 10A, in an exemplary embodiment, checking step 350 further includes a step 610 of suggesting a hierarchical assembly strategy, where the hierarchical assembly strategy is designed to mitigate the assembly piece incompatibility events. Referring to FIG. 10B, in an exemplary embodiment, checking step 350 further includes a step 620 of issuing a warning if at least one significant DNA sequence repeat exists in the plan.

Outputting

Figure 11A:
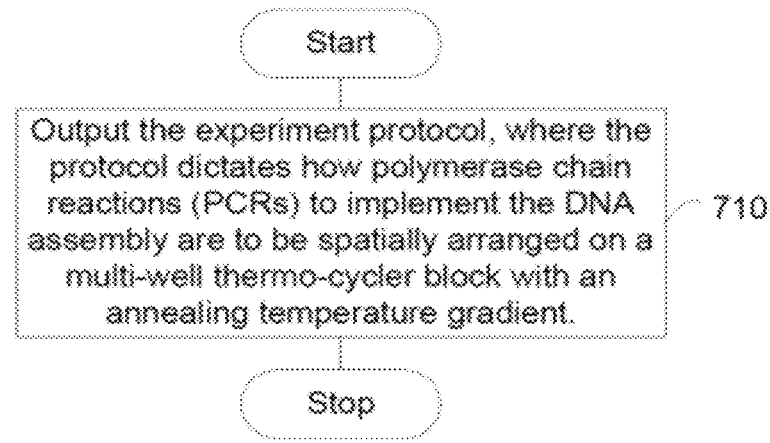
FIGS. 11A and 11B illustrate various components of one method used to design the DNA assembly process.
Figure 11B:
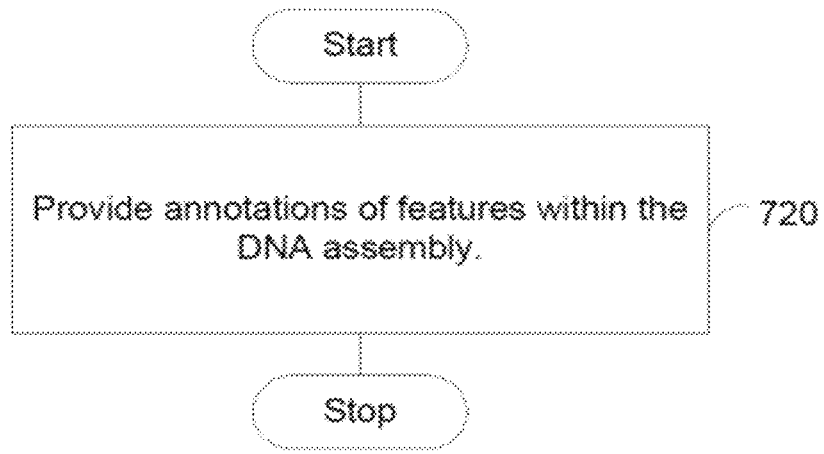

Referring to FIG. 11A, in an exemplary embodiment, outputting step 360 includes a step 710 of outputting the experiment protocol, where the protocol dictates how polymerase chain reactions (PCRs) to implement the DNA assembly are to be spatially arranged on a multi-well thermo-cycler block with an annealing temperature gradient. Referring to FIG. 11B, in an exemplary embodiment, outputting step 360 further includes a step 720 of providing annotations of features within the DNA assembly.

Direct Synthesis Pieces and DNA Oligonucleotides (Oligos)

Figure 12:
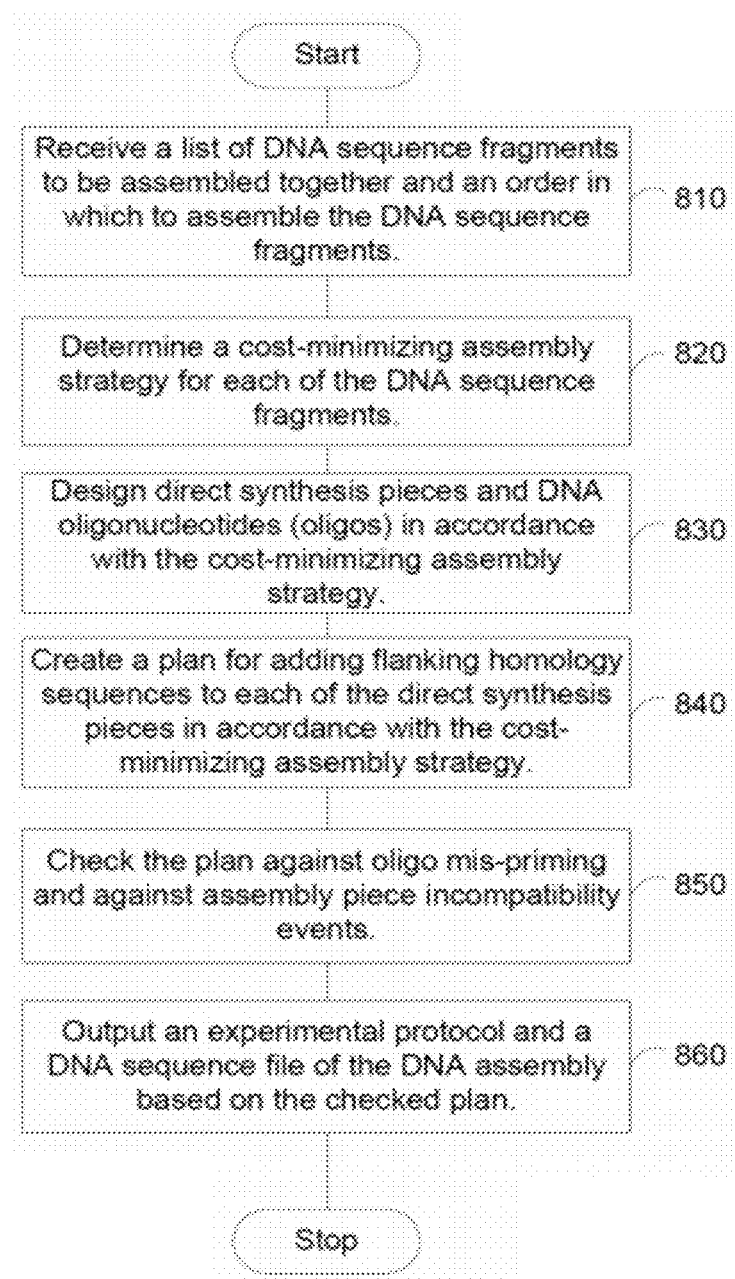
FIG. 12 illustrates one method used to design the DNA assembly process.

Referring to FIG. 12, in an exemplary embodiment, the assembly methods includes a step 810 of receiving a list of DNA sequence fragments to be assembled together and an order in which to assemble the DNA sequence fragments, a step 820 of determining a cost-minimizing assembly strategy for each of the DNA sequence fragments, a step 830 of designing direct synthesis pieces and DNA oligonucleotides (oligos) in accordance with the cost-minimizing assembly strategy, a step 840 of creating a plan for adding flanking homology sequences to each of the direct synthesis pieces in accordance with the cost-minimizing assembly strategy, a step 850 of checking the plan against oligo mis-priming and against assembly piece incompatibility events, and a step 860 of outputting an experimental protocol and a DNA sequence file of the DNA assembly based on the checked plan.

Receiving

Figure 13A:
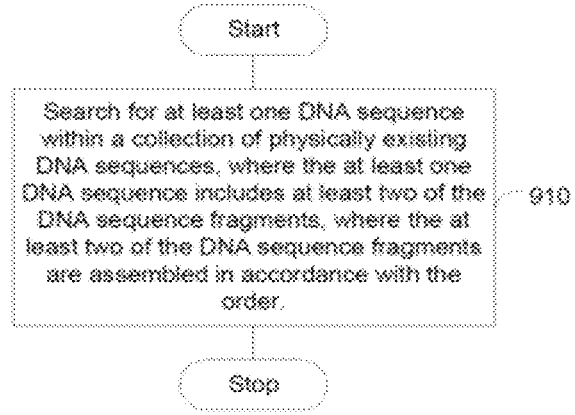
FIGS. 13A-13E illustrate various components of one method used to design the DNA assembly process.
Figure 13B:
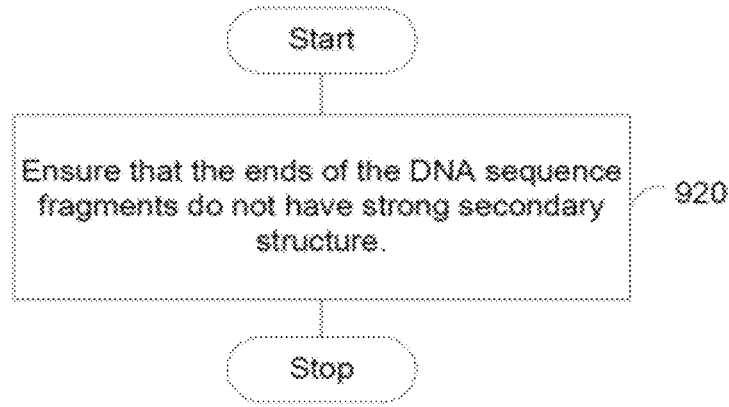

Referring to FIG. 13A, in an exemplary embodiment, receiving step 810 further includes a step 910 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 13B, in an exemplary embodiment, receiving step 810 further includes a step 920 of ensuring that the ends of the DNA sequence fragments do not have strong secondary structure.

Figure 13C:
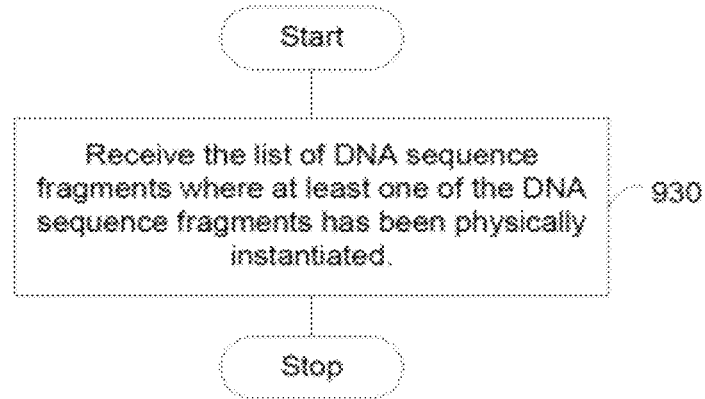
Figure 13D:
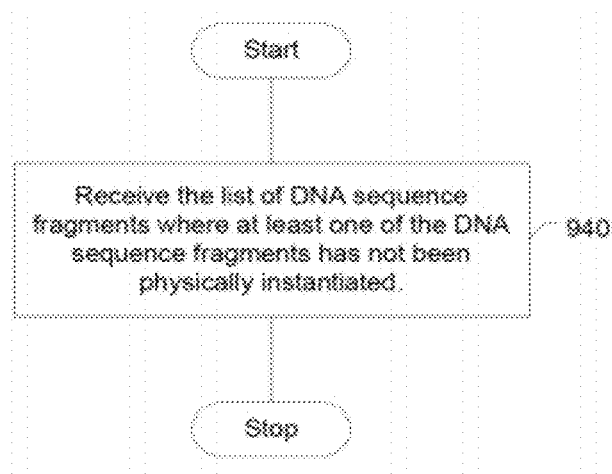
Figure 13E:
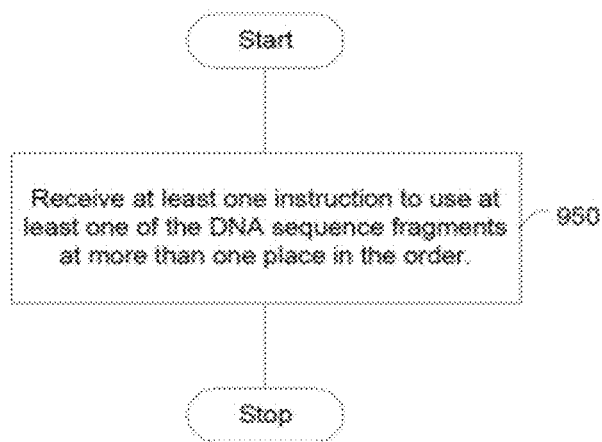

Referring to FIG. 13C, in an exemplary embodiment, receiving step 810 includes a step 930 of receiving the list of DNA sequence fragments where at least one of the DNA sequence fragments has been physically instantiated. Referring to FIG. 13D, in an exemplary embodiment, receiving step 810 includes a step 940 of receiving the list of DNA sequence fragments where at least one of the DNA sequence fragments has not been physically instantiated. Referring to FIG. 13E, in an exemplary embodiment, receiving step 810 includes a step 950 of receiving at least one instruction to use at least one of the DNA sequence fragments at more than one place in the order.

Creating

Figure 14A:
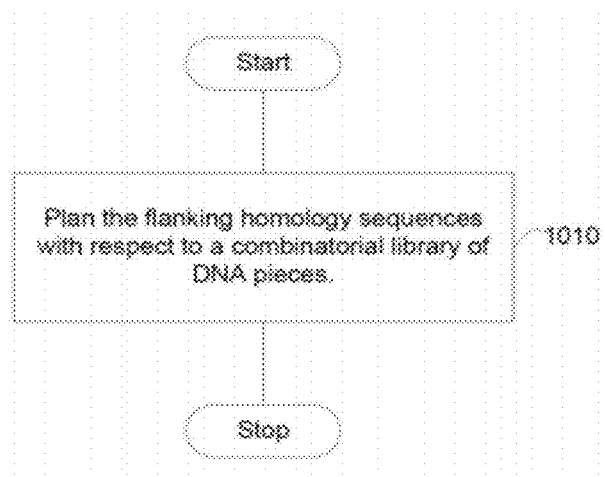
FIGS. 14A and 14B illustrate various components of one method used to design the DNA assembly process.
Figure 14B:
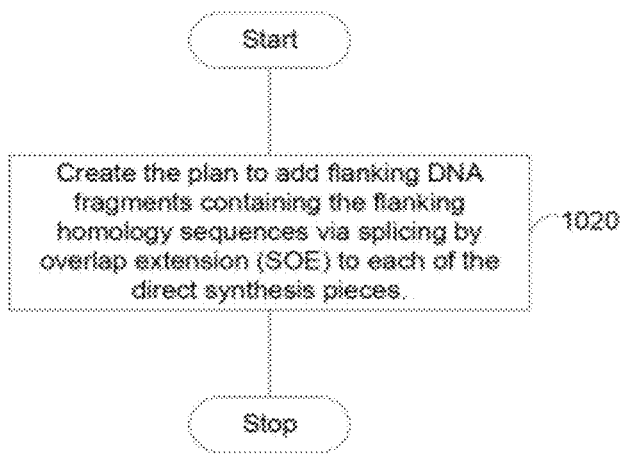

Referring to FIG. 14A, in an exemplary embodiment, creating step 840 includes a step 1010 of planning the flanking homology sequences with respect to a combinatorial library of DNA pieces. Referring to FIG. 14B, in an exemplary embodiment, creating step 840 includes a step 1020 of creating the plan to add flanking DNA fragments containing the flanking homology sequences via splicing by overlap extension (SOE) to each of the direct synthesis pieces.

Checking

Figure 15A:
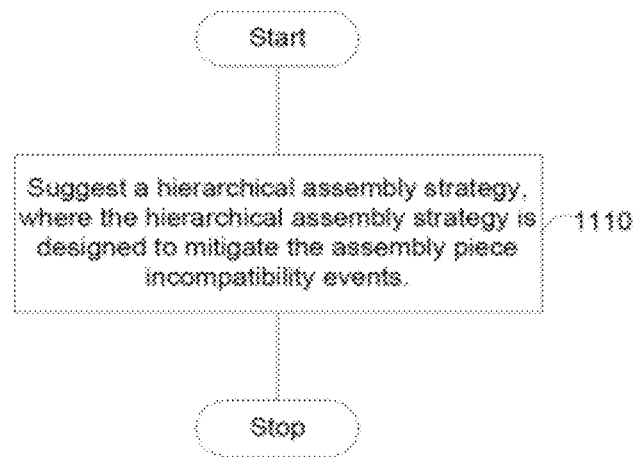
FIGS. 15A and 15B illustrate various components of one method used to design the DNA assembly process.
Figure 15B:
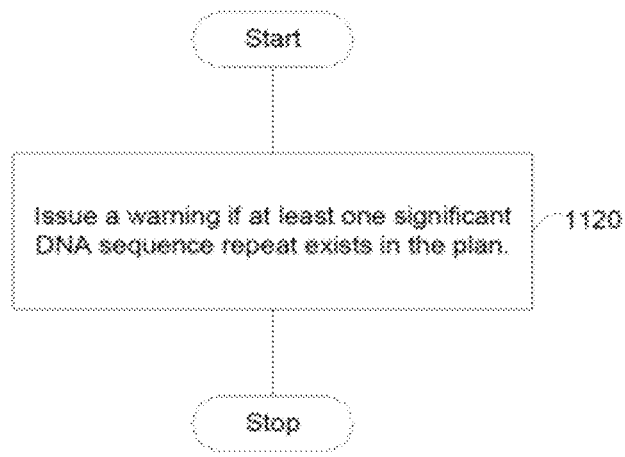

Referring to FIG. 15A, in an exemplary embodiment, checking step 850 further includes a step 1110 of suggesting a hierarchical assembly strategy, where the hierarchical assembly strategy is designed to mitigate the assembly piece incompatibility events. Referring to FIG. 15B, in an exemplary embodiment, checking step 850 further includes a step 1120 of issuing a warning if at least one significant DNA sequence repeat exists in the plan.

Outputting

Figure 16A:
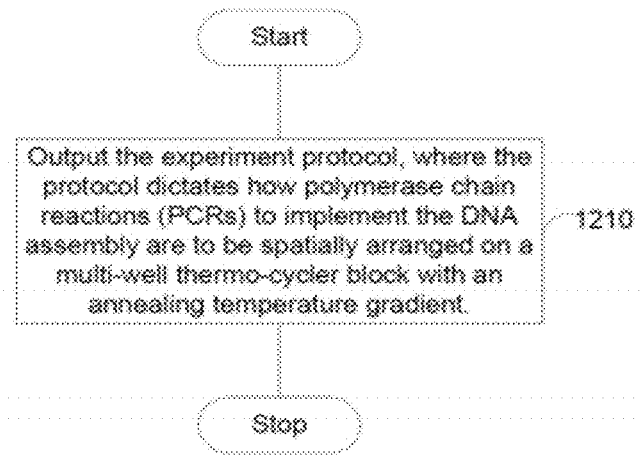
FIGS. 16A and 16B illustrate various components of one method used to design the DNA assembly process.
Figure 16B:
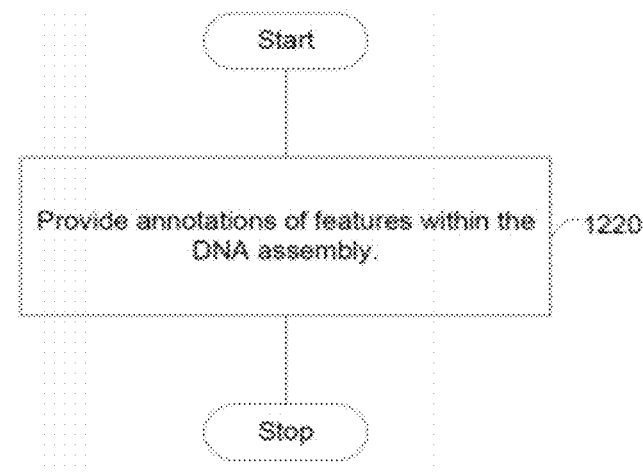

Referring to FIG. 16A, in an exemplary embodiment, outputting step 860 includes a step 1210 of outputting the experiment protocol, where the protocol dictates how polymerase chain reactions (PCRs) to implement the DNA assembly are to be spatially arranged on a multi-well thermo-cycler block with an annealing temperature gradient. Referring to FIG. 16B, in an exemplary embodiment, outputting step 860 further includes a step 1220 of providing annotations of features within the DNA assembly.

DNA Oligonucleotides (Oligos) and Direct Synthesis Pieces

Figure 17:
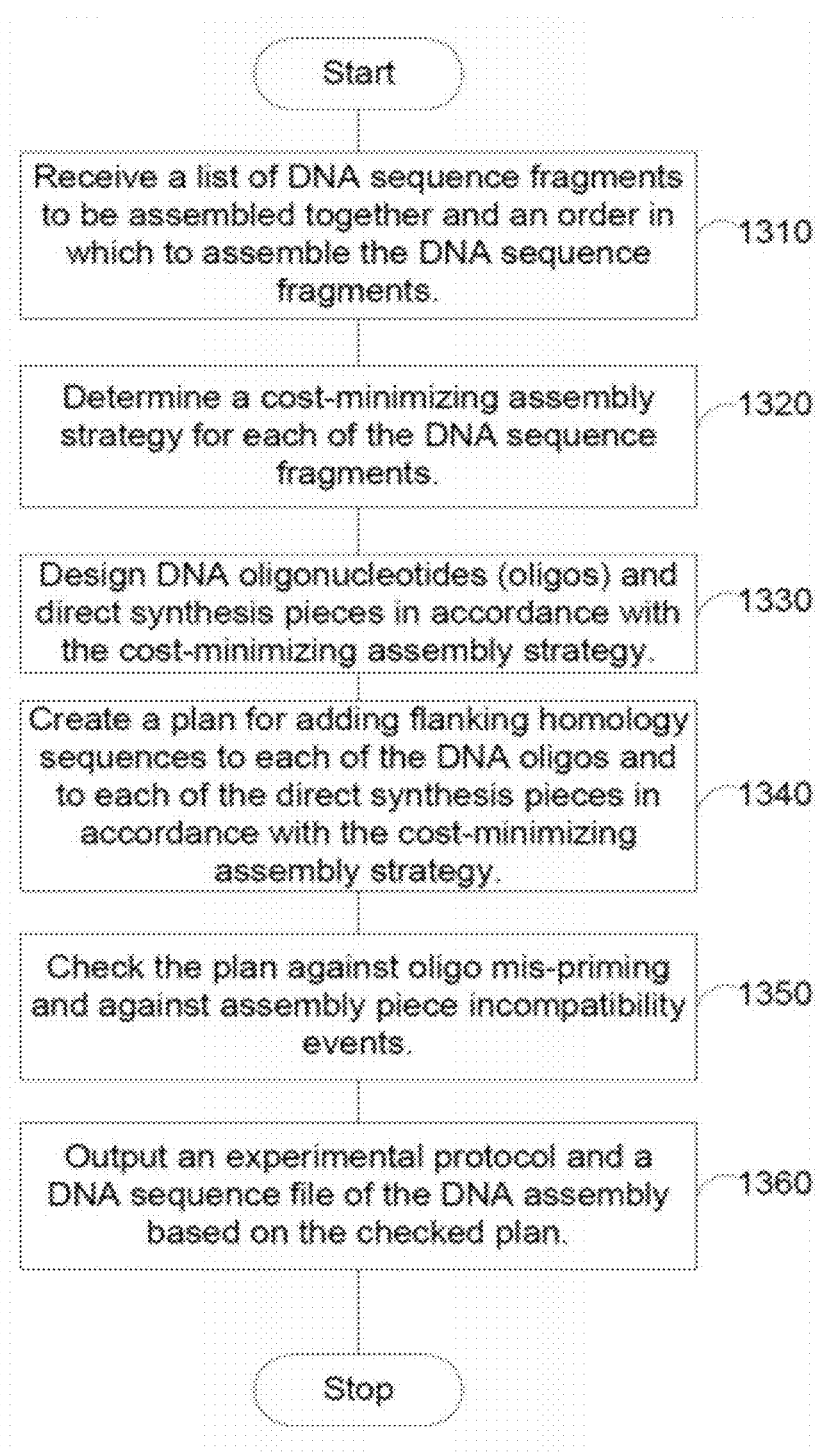
FIG. 17 illustrates one method used to design the DNA assembly process.

Referring to FIG. 17, in an exemplary embodiment, the present invention includes a step 1310 of receiving a list of DNA sequence fragments to be assembled together and an order in which to assemble the DNA sequence fragments, a step 1320 of determining a cost-minimizing assembly strategy for each of the DNA sequence fragments, a step 1330 of designing DNA oligonucleotides (oligos) and direct synthesis pieces in accordance with the cost-minimizing assembly strategy, a step 1340 of creating a plan for adding flanking homology sequences to each of the DNA oligos and to each of the direct synthesis pieces in accordance with the cost-minimizing assembly strategy, a step 1350 of checking the plan against oligo mis-priming and against assembly piece incompatibility events, and a step 1360 of outputting an experimental protocol and a DNA sequence file of the DNA assembly based on the checked plan.

Receiving

Figure 18A:
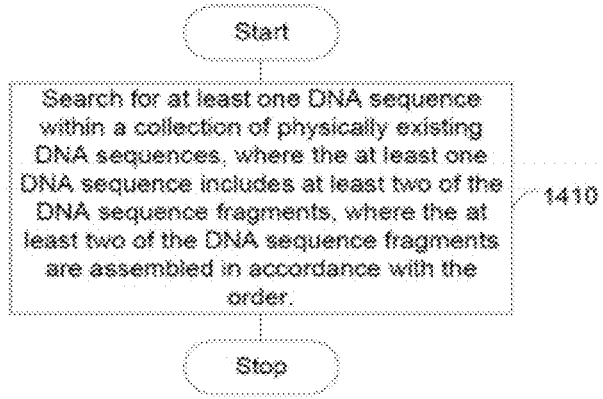
FIGS. 18A-18E illustrate various components of one method used to design the DNA assembly process
Figure 18B:
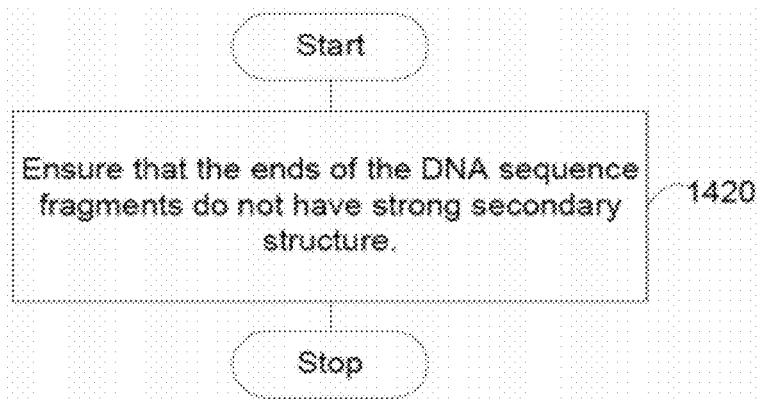

Referring to FIG. 18A, in an exemplary embodiment, receiving step 1310 further includes a step 1410 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 18B, in an exemplary embodiment, receiving step 1310 further includes a step 1420 of ensuring that the ends of the DNA sequence fragments do not have strong secondary structure.

Figure 18C:
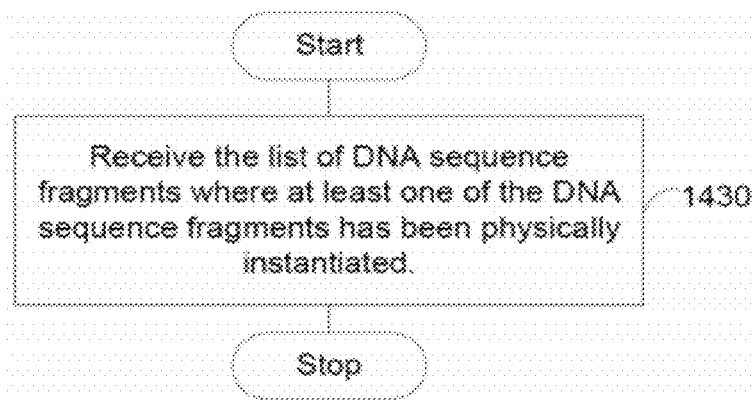
Figure 18D:
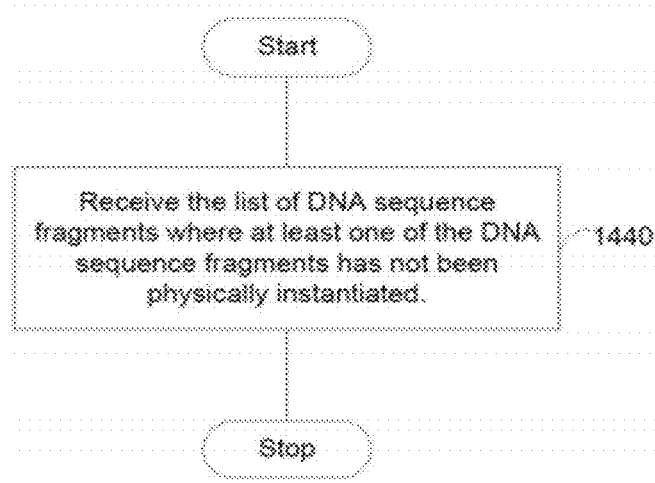
Figure 18E:
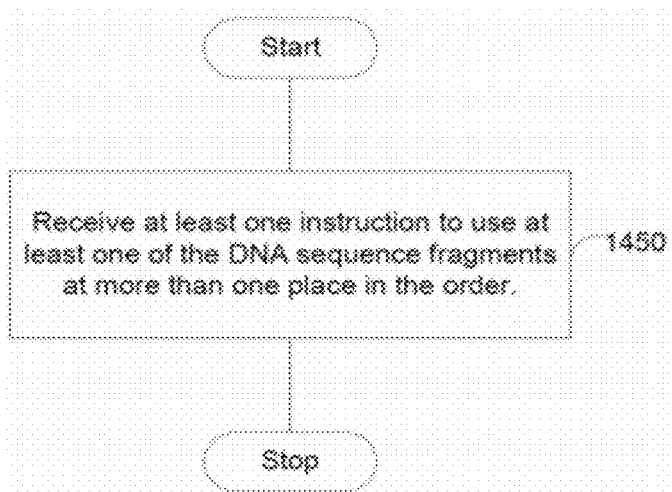

Referring to FIG. 18C, in an exemplary embodiment, receiving step 1310 includes a step 1430 of receiving the list of DNA sequence fragments where at least one of the DNA sequence fragments has been physically instantiated. Referring to FIG. 18D, in an exemplary embodiment, receiving step 1310 includes a step 1440 of receiving the list of DNA sequence fragments where at least one of the DNA sequence fragments has not been physically instantiated. Referring to FIG. 18E, in an exemplary embodiment, receiving step 1310 includes a step 1450 of receiving at least one instruction to use at least one of the DNA sequence fragments at more than one place in the order.

Creating

Figure 19A:
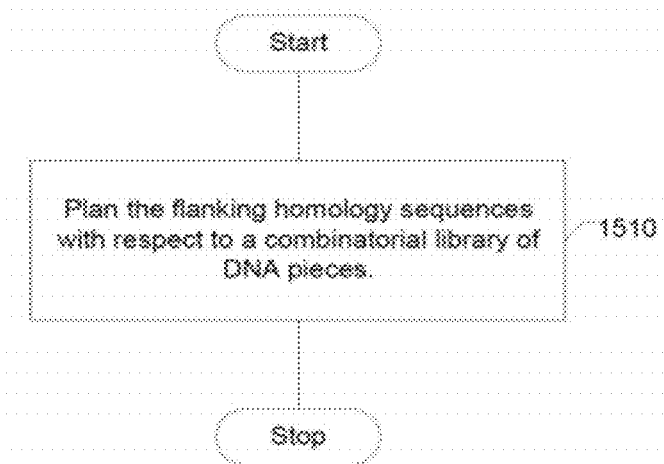
FIGS. 19A and 19B illustrate various components of one method used to design the DNA assembly process.
Figure 19B:
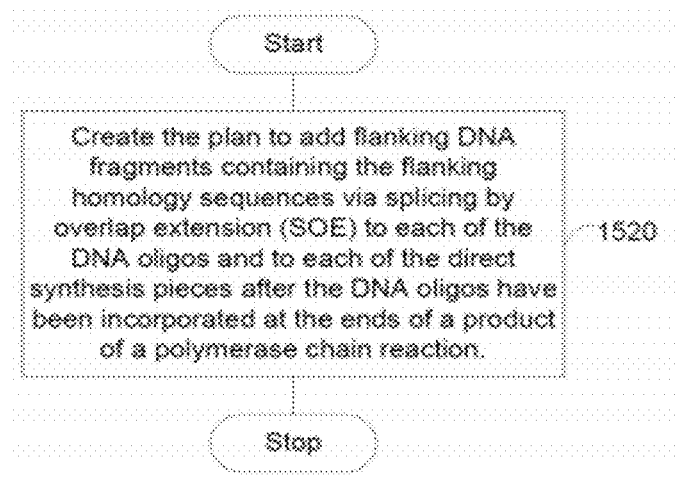

Referring to FIG. 19A, in an exemplary embodiment, creating step 1340 includes a step 1510 of planning the flanking homology sequences with respect to a combinatorial library of DNA pieces. Referring to FIG. 19B, in an exemplary embodiment, creating step 1340 includes a step 1520 of creating the plan to add flanking DNA fragments containing the flanking homology sequences via splicing by overlap extension (SOE) to each of the DNA oligos and to each of the direct synthesis pieces after the DNA oligos have been incorporated at the ends of a product of a polymerase chain reaction.

Checking

Figure 20A:
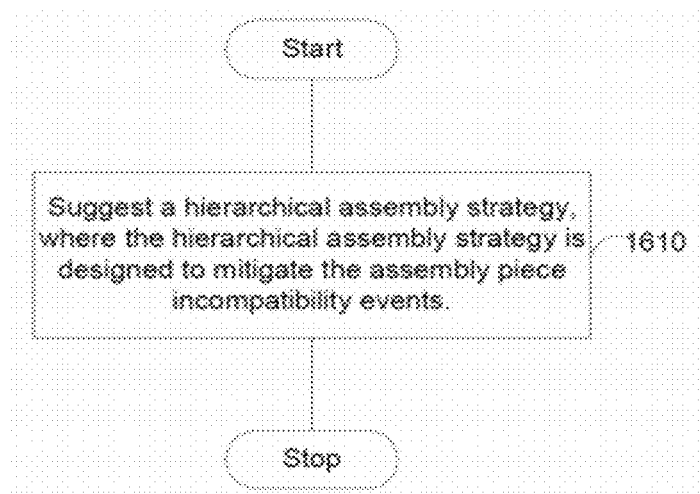
FIGS. 20A and 20B illustrate various components of one method used to design the DNA assembly process.
Figure 20B:
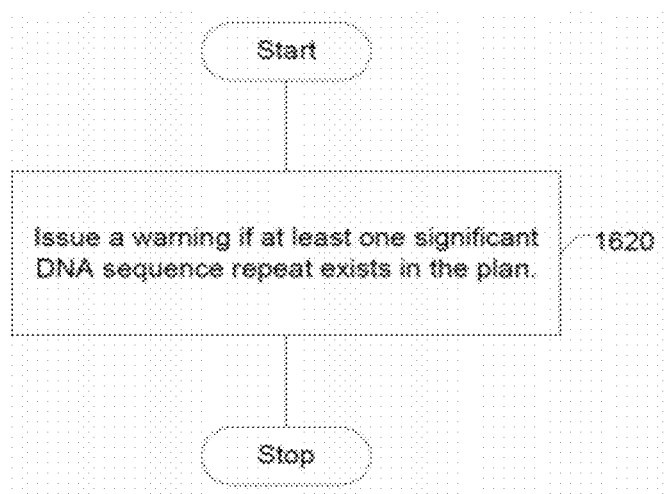

Referring to FIG. 20A, in an exemplary embodiment, checking step 1350 further includes a step 1610 of suggesting a hierarchical assembly strategy, where the hierarchical assembly strategy is designed to mitigate the assembly piece incompatibility events. Referring to FIG. 20B, in an exemplary embodiment, checking step 1350 further includes a step 1620 of issuing a warning if at least one significant DNA sequence repeat exists in the plan.

Outputting

Figure 21A:
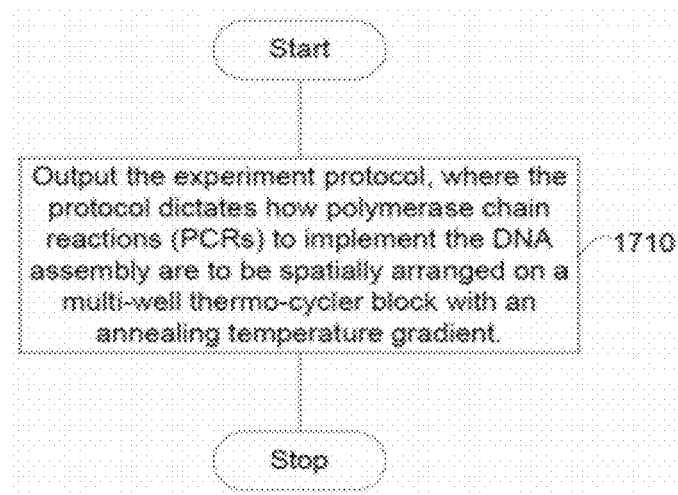
FIGS. 21A and 21B illustrate various components of one method used to design the DNA assembly process.
Figure 21B:
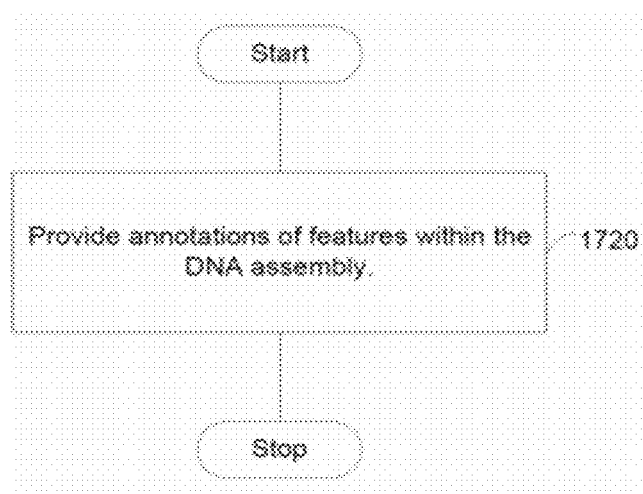

Referring to FIG. 21A, in an exemplary embodiment, outputting step 1360 includes a step 1710 of outputting the experiment protocol, where the protocol dictates how polymerase chain reactions (PCRs) to implement the DNA assembly are to be spatially arranged on a multi-well thermo-cycler block with an annealing temperature gradient. Referring to FIG. 21B, in an exemplary embodiment, outputting step 1360 further includes a step 1720 of providing annotations of features within the DNA assembly.

Optimized Overhang Sequences

Figure 22:
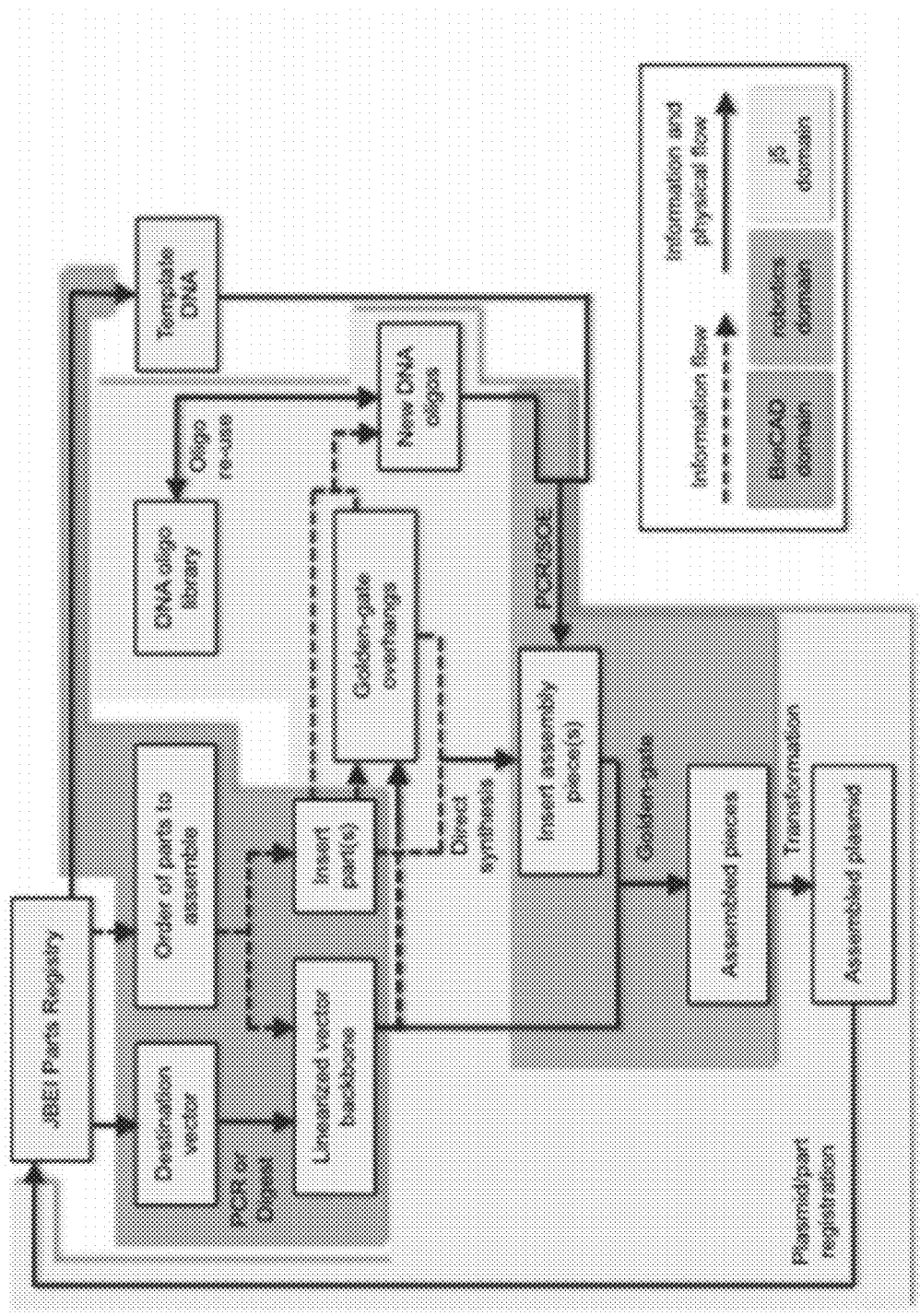
FIG. 22 illustrates a process flow of an exemplary embodiment of a method to design the DNA assembly process using optimized overhang sequences via Goldengate assembly.

FIG. 22 depicts a process flow of an exemplary embodiment of the present invention using optimized overhang sequences via Golden-gate assembly. In an exemplary embodiment, the present invention allows for the selection of parts to assemble from a Registry of Biological Parts (e.g., the JBEI Parts Registry) or a local collection of DNA sequences. In an exemplary embodiment, the present invention uses BioCAD (biological computer-aided design) tools in this process. Specifically, to the benefit of Golden-gate assembly, in an exemplary embodiment, the present invention uses BioCAD tools (1) to suggest viable alternatives to undesirable repeated homologous sequences (e.g., identifying two distinct terminators with comparable function), (2) to suggest point mutations to make that disrupt internal BioBrick/BsaI restriction sites, and (3) to query collections of DNA sequences for physically existing and available sequences that already contain two or more of the parts to be assembled together in the proper order and proper orientation, thereby reducing redundant fragment assembly steps where at all possible. The present invention then categorizes the parts to be assembled into either the linearized destination vector, or insert parts. The linearized destination vector is nominally physically achieved by digesting the destination vector with restriction enzymes or by PCR-amplifying the vector backbone, although direct DNA synthesis of an entire vector backbone could be done as well.

Given the sequences of the linearized vector backbone and the insert parts, in certain embodiments, the method designs 4 bp overhang sequences for each assembly piece, and performs an analysis to determine for which, if any, portions of the assembly direct synthesis would be more cost-effective than either PCR/SOE or oligo embedding. The method then designs DNA oligos for synthesis, and/or suggests re-use of existing oligos where possible, to amplify the desired assembly pieces. Notably, the vector backbone and/or any of the insert parts to be assembled do not necessarily need to physically exist (a prerequisite endonuclease digestion or PCR amplification) before the method is used to design the assembly, since it is possible to specify a direct synthesis strategy for any assembly fragment.

The method allows for liquid handling robotics or other devices to assist the execution of PCR/SOE to generate the assembly pieces, as well as their subsequent SLIC/Gibson/CPEC assembly. The method facilitates this process by condensing/aggregating designs for multiple independent assemblies (into 96-well plate format (or other formats), including optimally distributing reactions across a thermocycler annealing temperature gradient. After transforming a competent cloning strain with the assembly reaction, the present invention sequence verifies a clonal isolate of the assembled plasmid, and deposits the clonal isolate into the parts registry or local collection for subsequent re-use.

In certain embodiments, when designing Golden-gate assemblies, the method assumes that there are no internal BsaI sites in any of the DNA fragments to be assembled.

DNA Oligonucleotides (Oligos)

Figure 23:
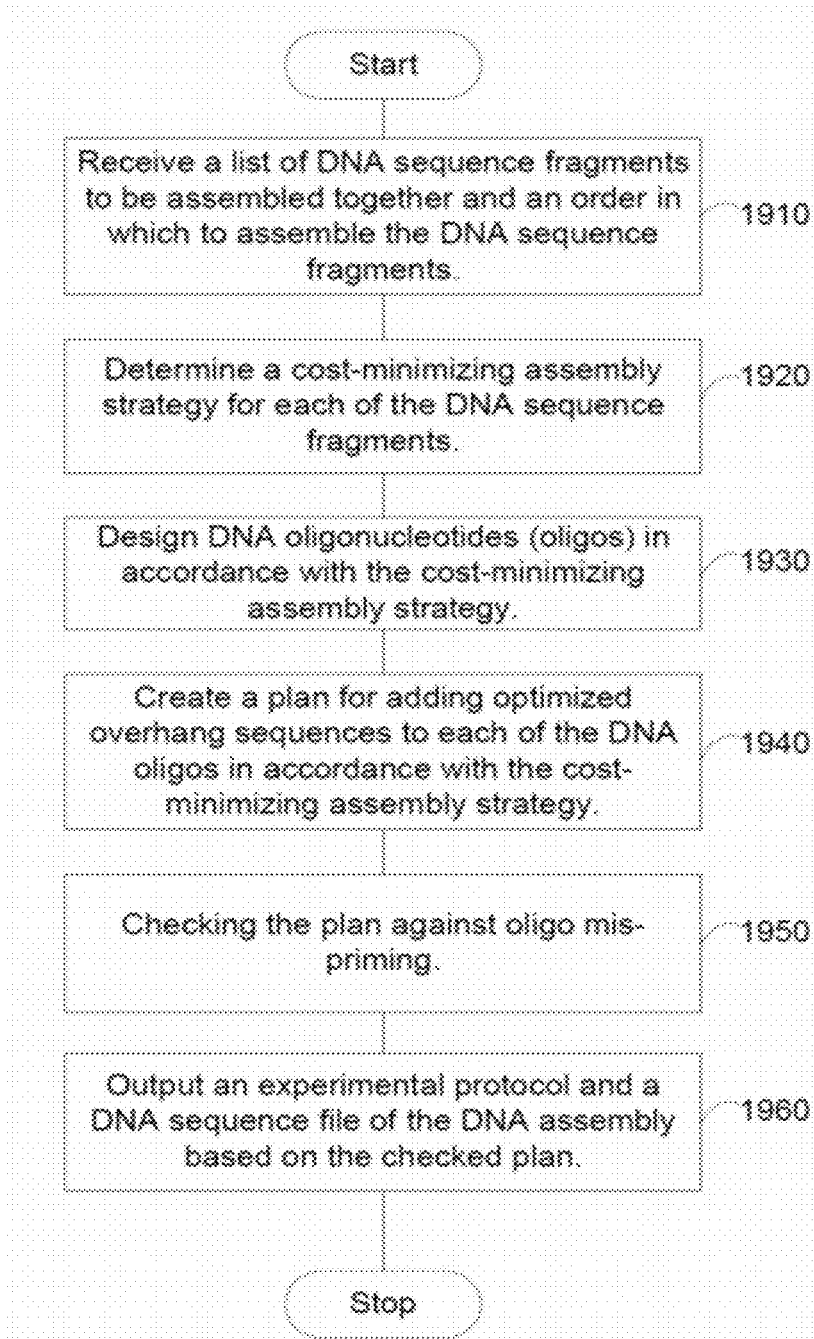
FIG. 23 illustrates one method used to design the DNA assembly process.

Referring to FIG. 23, in an exemplary embodiment, the present invention includes a step 1910 of receiving a list of DNA sequence fragments to be assembled together and an order in which to assemble the DNA sequence fragments, a step 1920 of determining a cost-minimizing assembly strategy for each of the DNA sequence fragments, a step 1930 of designing DNA oligonucleotides (oligos) in accordance with the cost-minimizing assembly strategy, a step 1940 of creating a plan for adding optimized overhang sequences to each of the DNA oligos in accordance with the cost-minimizing assembly strategy, a step 1950 of checking the plan against oligo mis-priming, and a step 1960 of outputting an experimental protocol and a DNA sequence file of the DNA assembly based on the checked plan.

Receiving

Figure 24A:
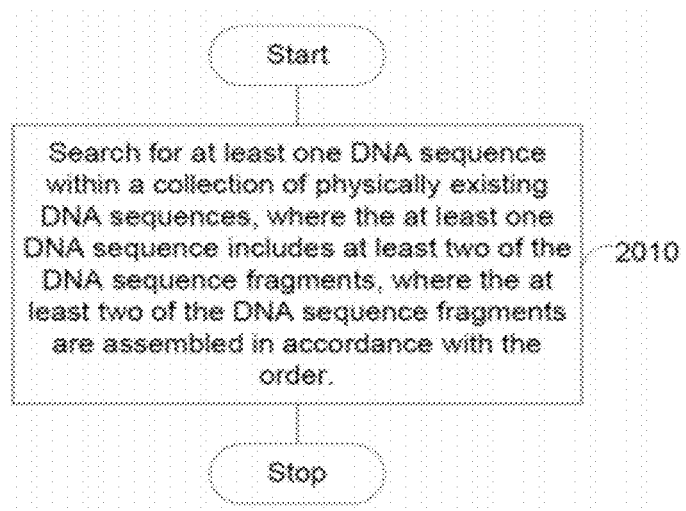
FIGS. 24A-24D illustrate various components of one method used to design the DNA assembly process.
Figure 24B:
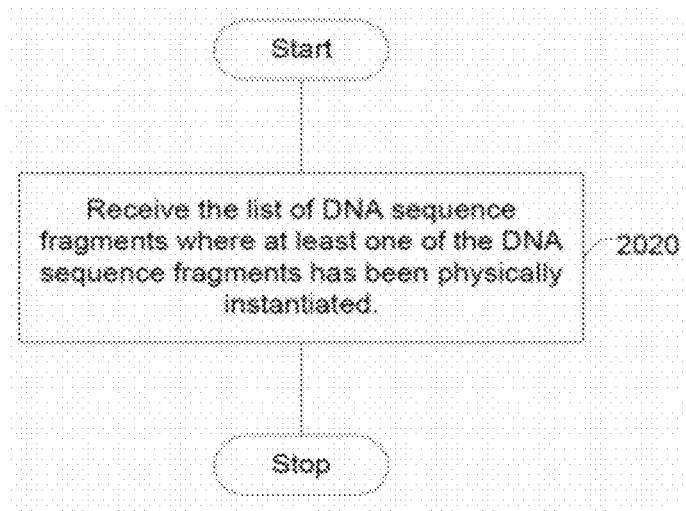
Figure 24C:
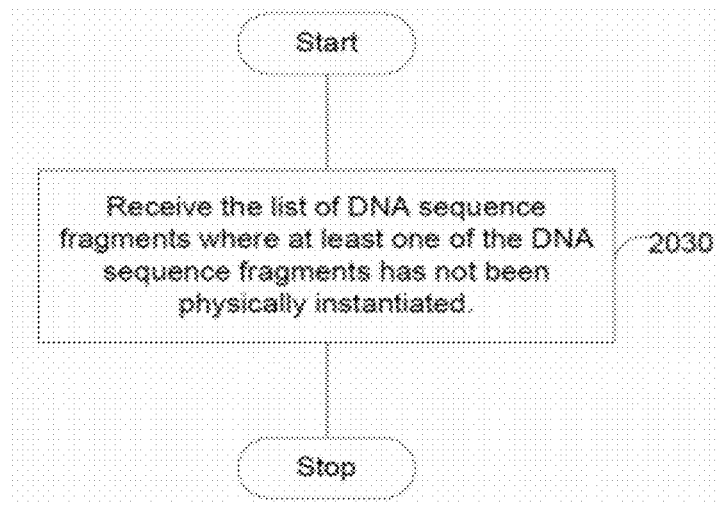
Figure 24D:
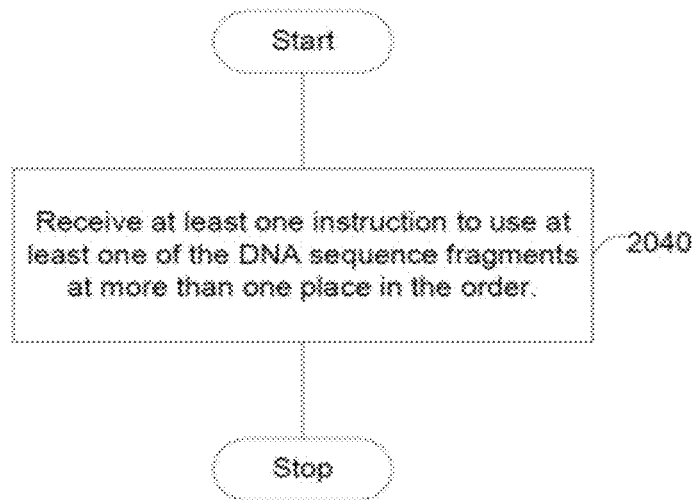

Referring to FIG. 24A, in an exemplary embodiment, receiving step 1910 further includes a step 2010 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 24B, in an exemplary embodiment, receiving step 1910 includes a step 2020 of receiving the list of DNA sequence fragments where at least one of the DNA sequence fragments has been physically instantiated. Referring to FIG. 24C, in an exemplary embodiment, receiving step 1910 includes a step 2030 of receiving the list of DNA sequence fragments where at least one of the DNA sequence fragments has not been physically instantiated. Referring to FIG. 24D, in an exemplary embodiment, receiving step 1910 includes a step 2040 of receiving at least one instruction to use at least one of the DNA sequence fragments at more than one place in the order.

Creating

Figure 25A:
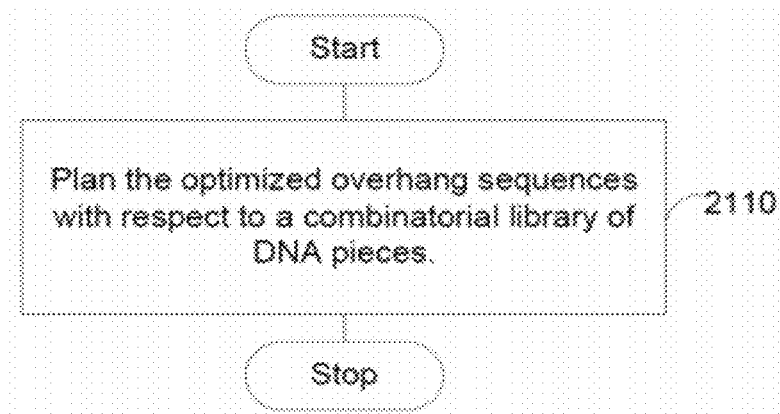
FIGS. 25A-25C illustrate various components of one method used to design the DNA assembly process.
Figure 25B:
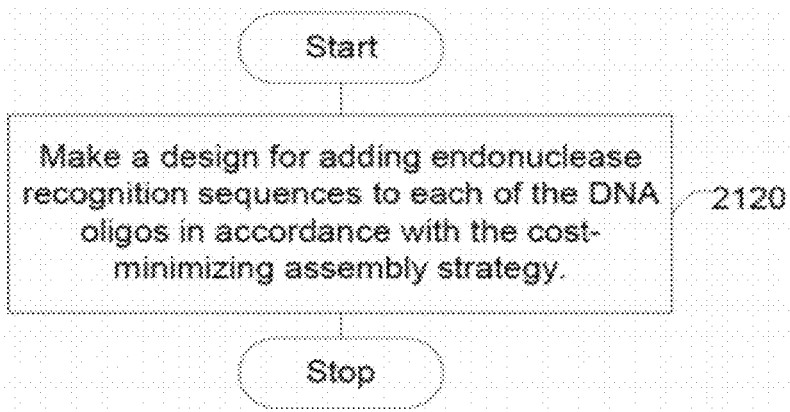
Figure 25C:
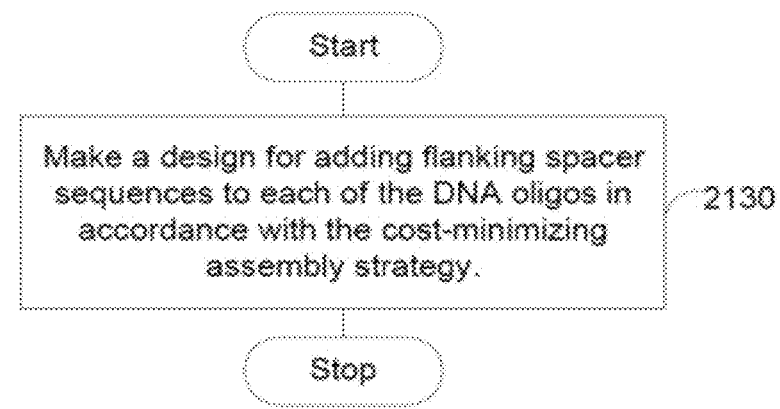

Referring to FIG. 25A, in an exemplary embodiment, creating step 1940 includes a step 2110 of planning the optimized overhang sequences with respect to a combinatorial library of DNA pieces. Referring to FIG. 25B, in an exemplary embodiment, creating step 1940 further includes a step 2120 of making a design for adding endonuclease recognition sequences to each of the DNA oligos in accordance with the cost-minimizing assembly strategy. Referring to FIG. 25C, in an exemplary embodiment, creating step 1940 further includes a step 2130 of making a design for adding flanking spacer sequences to each of the DNA oligos in accordance with the cost-minimizing assembly strategy.

Checking

Figure 26A:
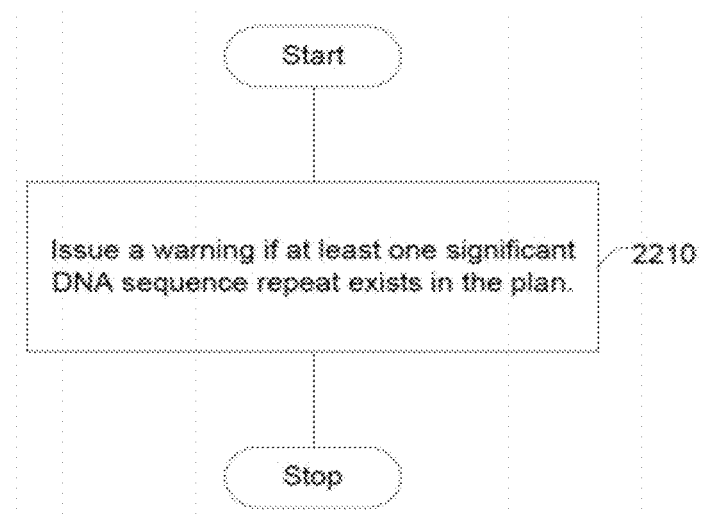
FIGS. 26A and 26B illustrate various components of one method used to design the DNA assembly process.
Figure 26B:
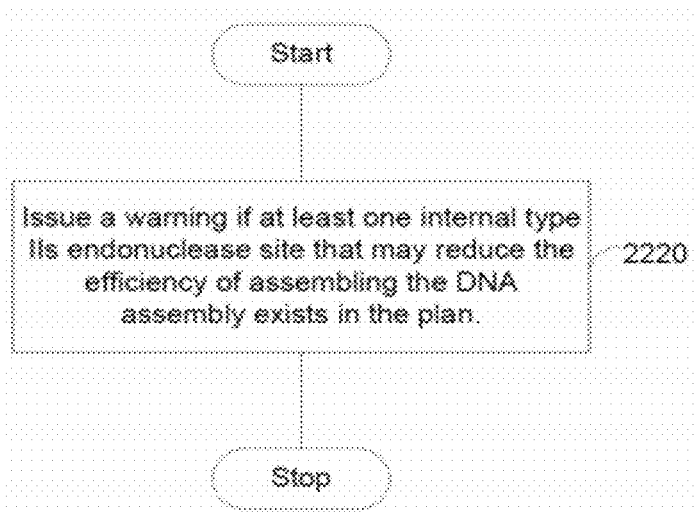

Referring to FIG. 26A, in an exemplary embodiment, checking step 1950 further includes a step 2210 of issuing a warning if at least one significant DNA sequence repeat exists in the plan. Referring to FIG. 26B, in an exemplary embodiment, checking step 1950 further includes a step 2220 of issuing a warning if at least one internal type Hs endonuclease site that may reduce the efficiency of assembling the DNA assembly exists in the plan.

Outputting

Figure 27A:
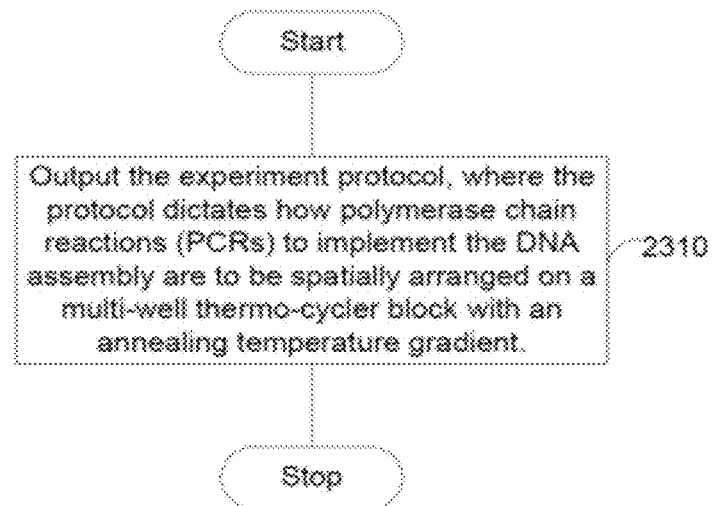
FIGS. 27 and 27B illustrate various components of one method used to design the DNA assembly process.
Figure 27B:
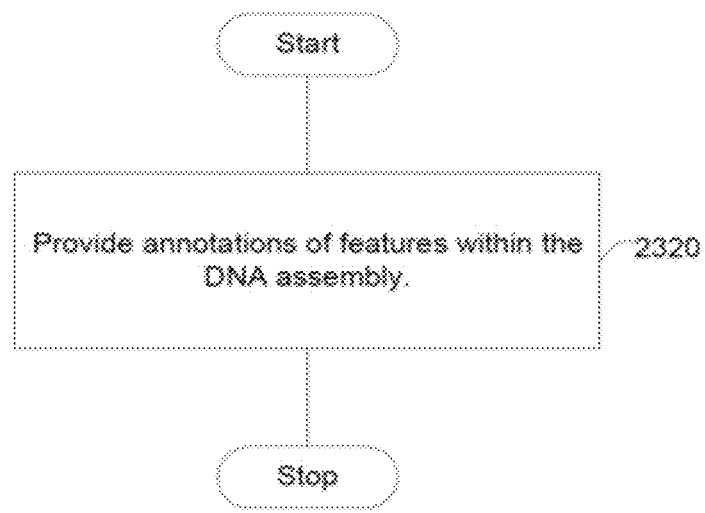

Referring to FIG. 27A, in an exemplary embodiment, outputting step 1960 includes a step 2310 of outputting the experiment protocol, where the protocol dictates how polymerase chain reactions (PCRs) to implement the DNA assembly are to be spatially arranged on a multi-well thermo-cycler block with an annealing temperature gradient. Referring to FIG. 27B, in an exemplary embodiment, outputting step 1960 further includes a step 2320 of providing annotations of features within the DNA assembly.

Direct Synthesis Pieces and DNA Oligonucleotides (Oligos)

Figure 28:
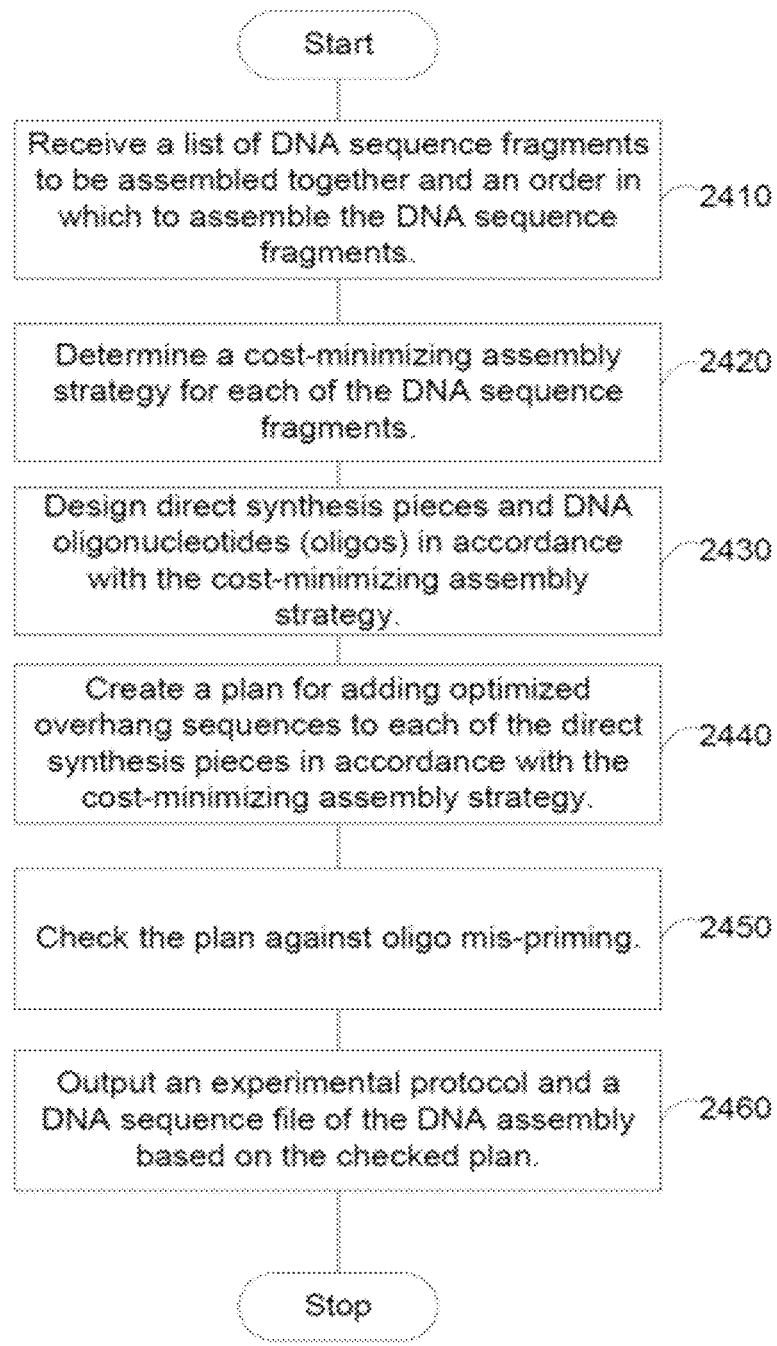
FIG. 28 illustrates one method used to design the DNA assembly process.

Referring to FIG. 28, in an exemplary embodiment, the present invention includes a step 2410 of receiving a list of DNA sequence fragments to be assembled together and an order in which to assemble the DNA sequence fragments, a step 2420 of determining a cost-minimizing assembly strategy for each of the DNA sequence fragments, a step 2430 of designing direct synthesis pieces and DNA oligonucleotides (oligos) in accordance with the cost-minimizing assembly strategy, a step 2440 of creating a plan for adding optimized overhang sequences to each of the direct synthesis pieces in accordance with the cost-minimizing assembly strategy, a step 2450 of checking the plan against oligo mis-priming, and step 2460 of outputting an experimental protocol and a DNA sequence file of the DNA assembly based on the checked plan.

Receiving

Figure 29A:
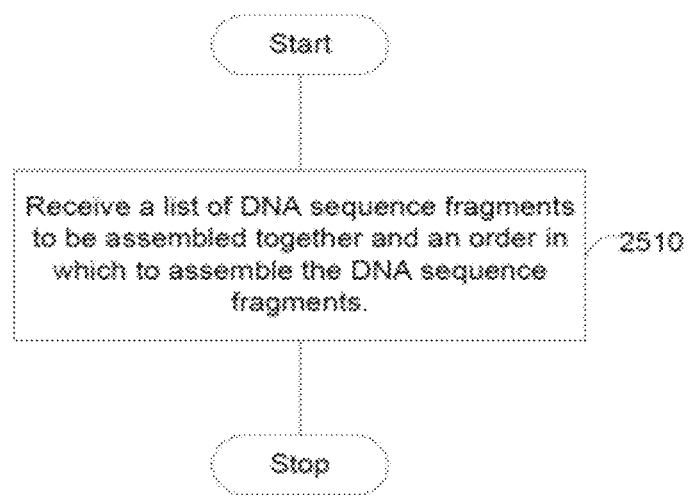
FIGS. 29A-29D illustrate various components of one method used to design the DNA assembly process.
Figure 29B:
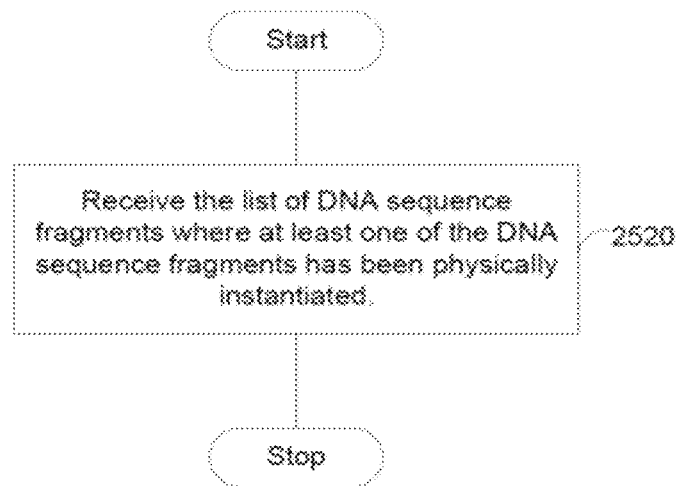
Figure 29C:
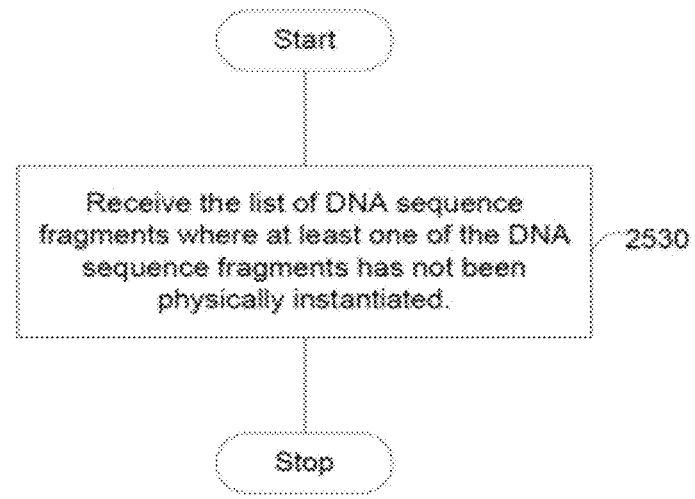
Figure 29D:
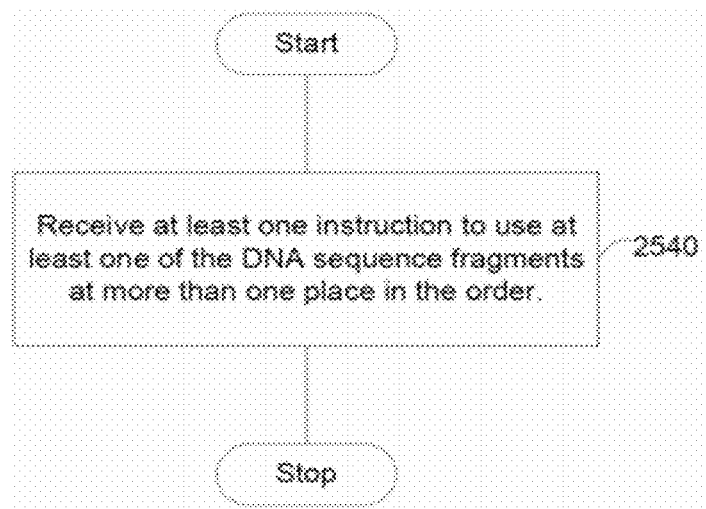

Referring to FIG. 29A, in an exemplary embodiment, receiving step 2410 further includes a step 2510 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 29B, in an exemplary embodiment, receiving step 2410 includes a step 2520 of receiving the list of DNA sequence fragments where at least one of the DNA sequence fragments has been physically instantiated. Referring to FIG. 29C, in an exemplary embodiment, receiving step 2410 includes a step 2530 of receiving the list of DNA sequence fragments where at least one of the DNA sequence fragments has not been physically instantiated. Referring to FIG. 29D, in an exemplary embodiment, receiving step 2410 includes a step 2540 of receiving at least one instruction to use at least one of the DNA sequence fragments at more than one place in the order.

Creating

Figure 30A:
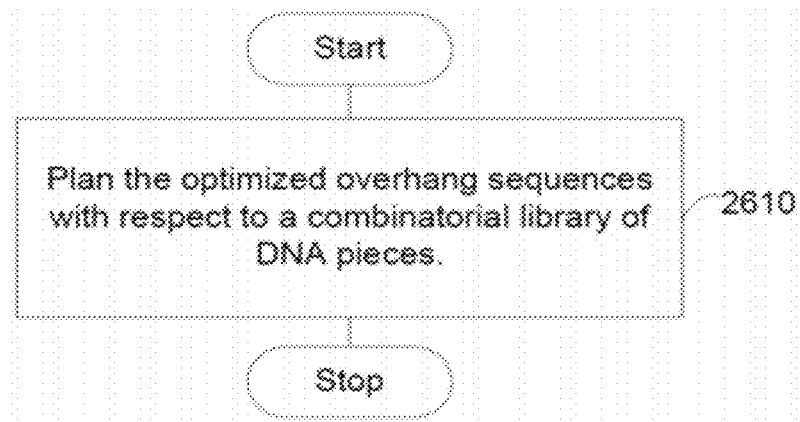
FIGS. 30A-30C illustrate various components of one method used to design the DNA assembly process.
Figure 30B:
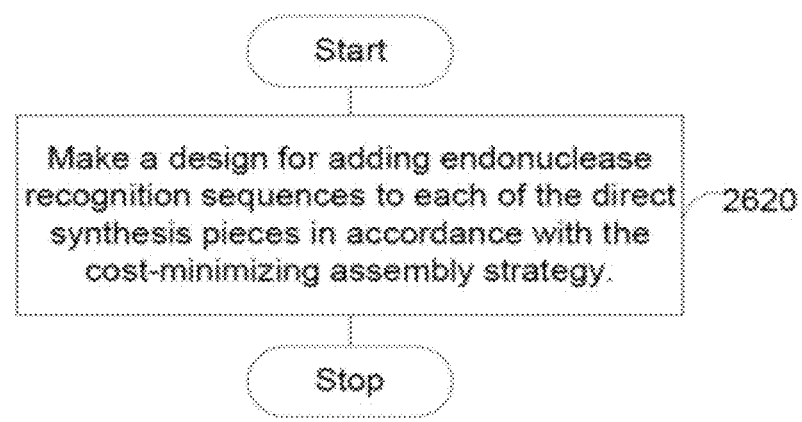
Figure 30C:
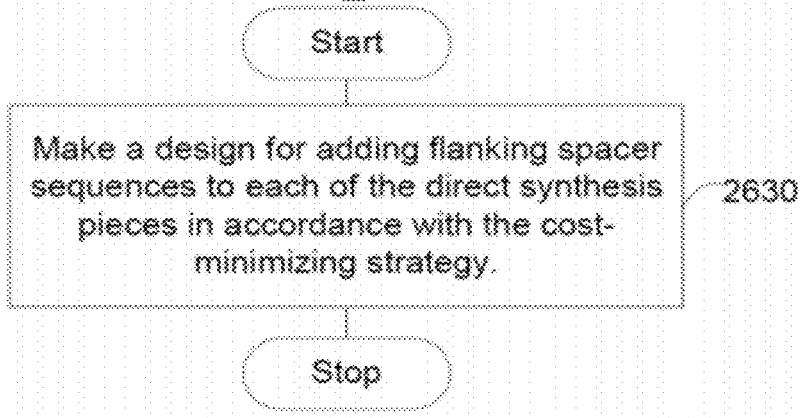

Referring to FIG. 30A, in an exemplary embodiment, creating step 2440 includes a step 2610 of planning the optimized overhang sequences with respect to a combinatorial library of DNA pieces. Referring to FIG. 30B, in an exemplary embodiment, creating step 2440 further includes a step 2620 of making a design for adding endonuclease recognition sequences to each of the direct synthesis pieces in accordance with the cost-minimizing assembly strategy. Referring to FIG. 30C, in an exemplary embodiment, creating step 2440 further includes a step 2630 of making a design for adding flanking spacer sequences to each of the direct synthesis pieces in accordance with the cost-minimizing strategy.

Checking

Figure 31A:
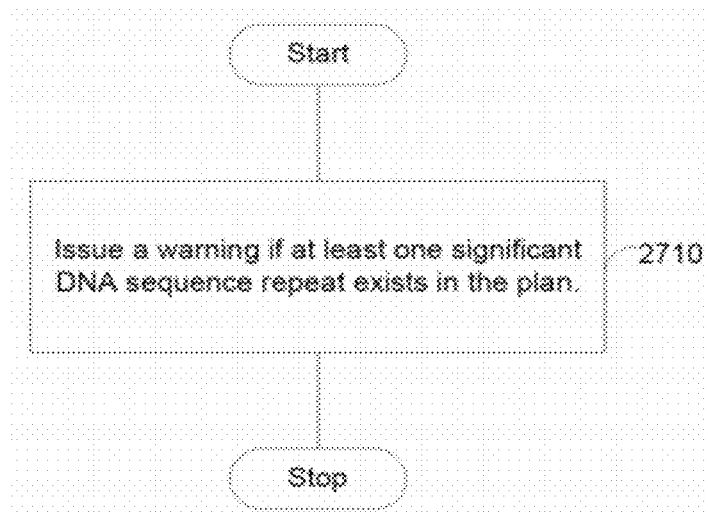
FIGS. 31A and 31B illustrate various components of one method used to design the DNA assembly process.
Figure 31B:
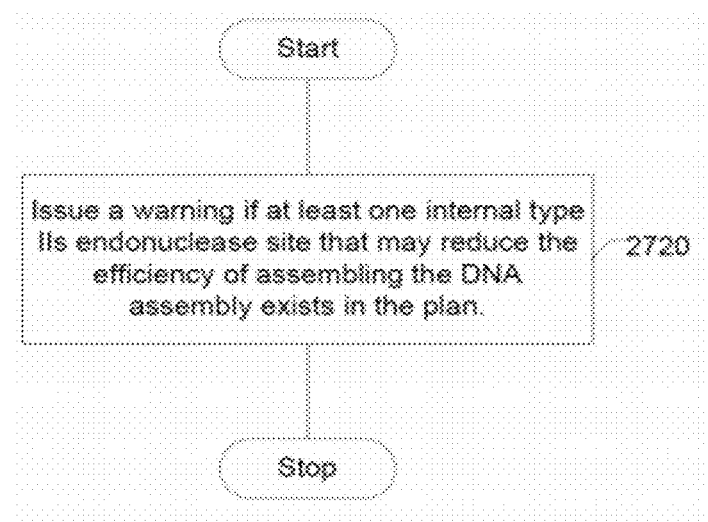

Referring to FIG. 31A, in an exemplary embodiment, checking step 2450 further includes a step 2710 of issuing a warning if at least one significant DNA sequence repeat exists in the plan. Referring to FIG. 31B, in an exemplary embodiment, checking step 2450 further includes a step 2720 of issuing a warning if at least one internal type Hs endonuclease site that may reduce the efficiency of assembling the DNA assembly exists in the plan.

Outputting

Figure 32A:
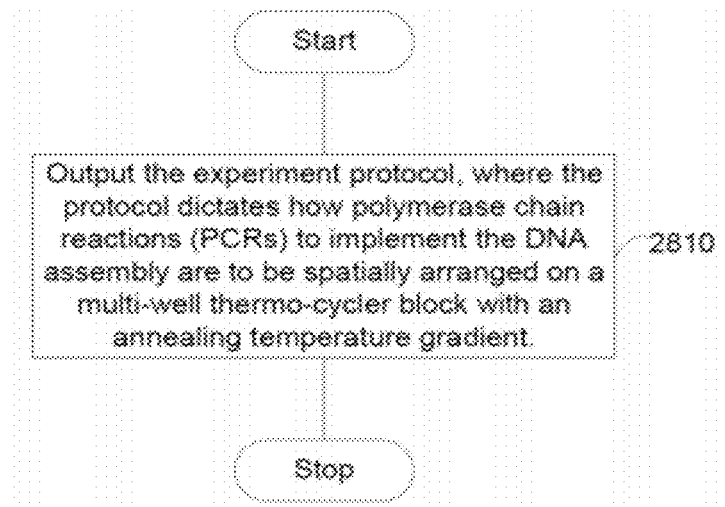
FIGS. 32A and 32B illustrate various components of one method used to design the DNA assembly process.
Figure 32B:
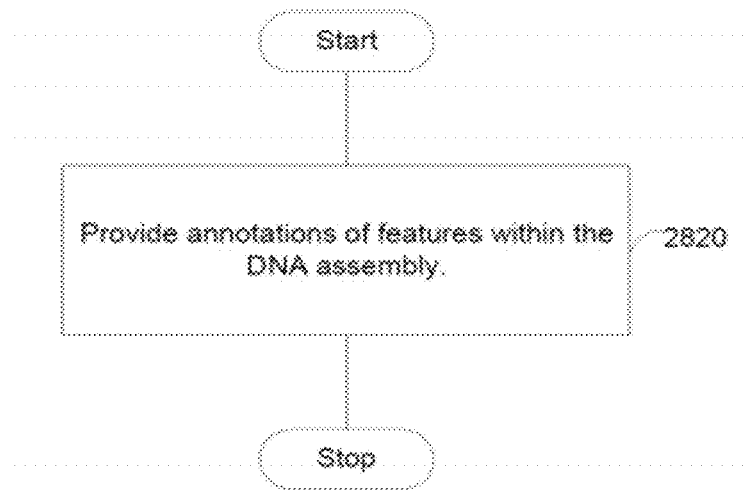

Referring to FIG. 32A, in an exemplary embodiment, outputting step 2460 includes a step 2810 of outputting the experiment protocol, where the protocol dictates how polymerase chain reactions (PCRs) to implement the DNA assembly are to be spatially arranged on a multi-well thermo-cycler block with an annealing temperature gradient. Referring to FIG. 32B, in an exemplary embodiment, outputting step 2460 further includes a step 2820 of providing annotations of features within the DNA assembly.

DNA Oligonucleotides (Oligos) and Direct Synthesis Pieces

Figure 33:
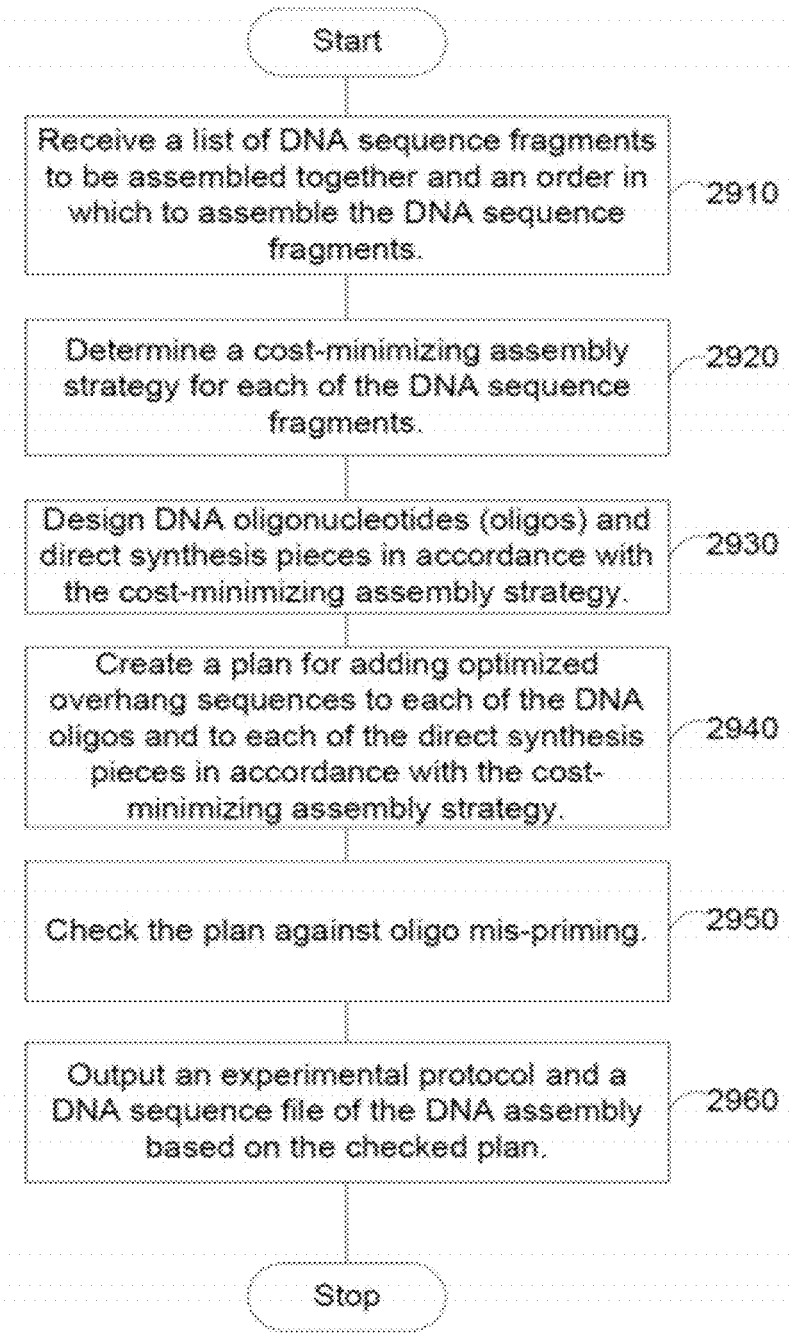
FIG. 33 illustrates one method used to design the DNA assembly process.

Referring to FIG. 33, in an exemplary embodiment, the present invention includes a step 2910 of receiving a list of DNA sequence fragments to be assembled together and an order in which to assemble the DNA sequence fragments, a step 2920 of determining a cost-minimizing assembly strategy for each of the DNA sequence fragments, a step 2930 of designing DNA oligonucleotides (oligos) and direct synthesis pieces in accordance with the cost-minimizing assembly strategy, a step 2940 of creating a plan for adding optimized overhang sequences to each of the DNA oligos and to each of the direct synthesis pieces in accordance with the cost-minimizing assembly strategy, a step 2950 of checking the plan against oligo mis-priming, and a step 2960 of outputting an experimental protocol and a DNA sequence file of the DNA assembly based on the checked plan.

Receiving

Figure 34A:
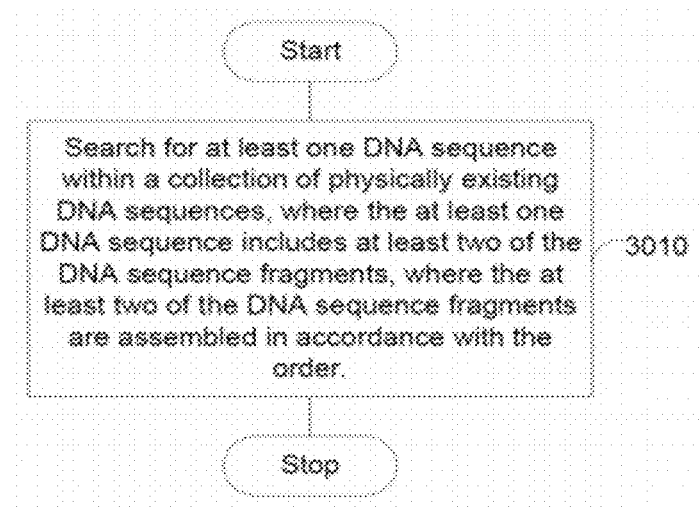
FIGS. 34A-34D illustrate various components of one method used to design the DNA assembly process.
Figure 34B:
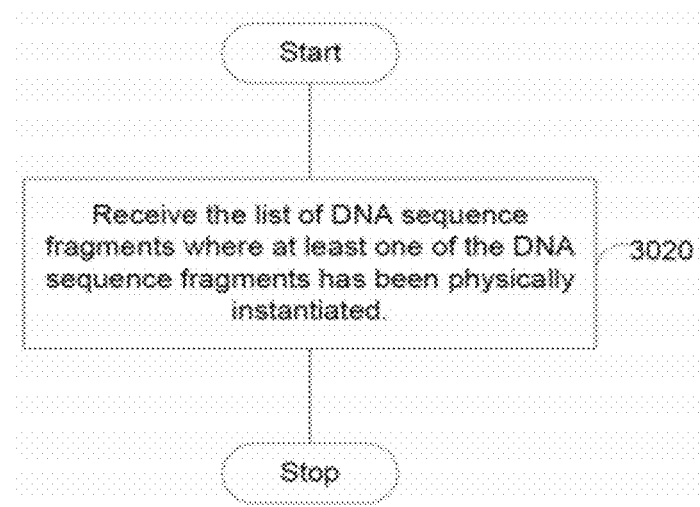
Figure 34C:
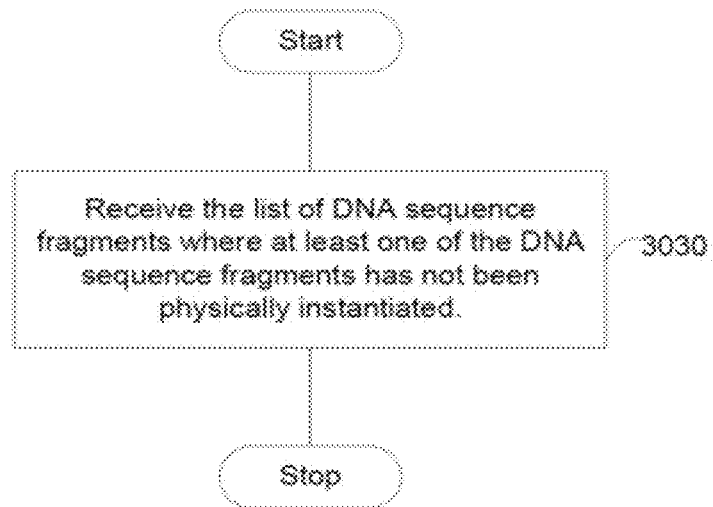
Figure 34D:
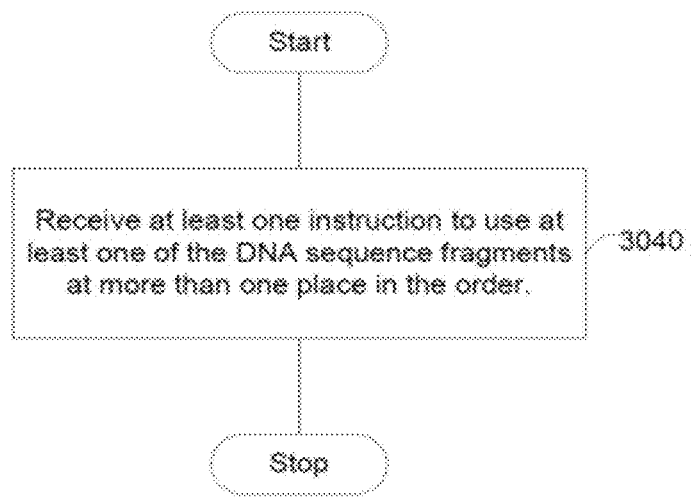

Referring to FIG. 34A, in an exemplary embodiment, receiving step 2910 further includes a step 3010 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 34B, in an exemplary embodiment, receiving step 2910 includes a step 3020 of receiving the list of DNA sequence fragments where at least one of the DNA sequence fragments has been physically instantiated. Referring to FIG. 34C, in an exemplary embodiment, receiving step 2910 includes a step 3030 of receiving the list of DNA sequence fragments where at least one of the DNA sequence fragments has not been physically instantiated. Referring to FIG. 34D, in an exemplary embodiment, receiving step 2910 includes a step 3040 of receiving at least one instruction to use at least one of the DNA sequence fragments at more than one place in the order.

Creating

Figure 35A:
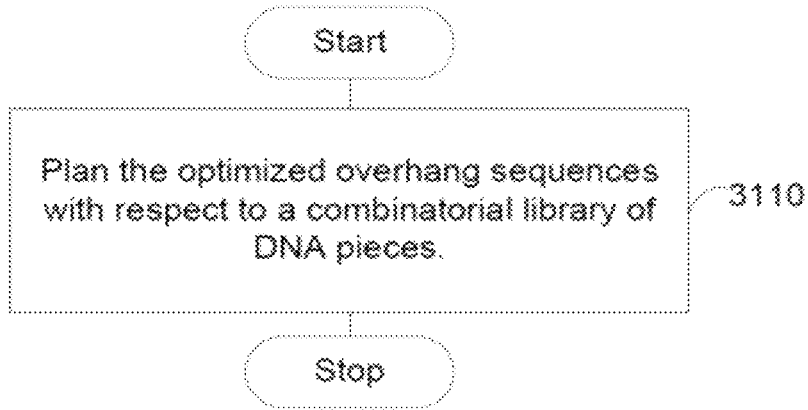
FIGS. 35A-35C illustrate various components of one method used to design the DNA assembly process.
Figure 35B:
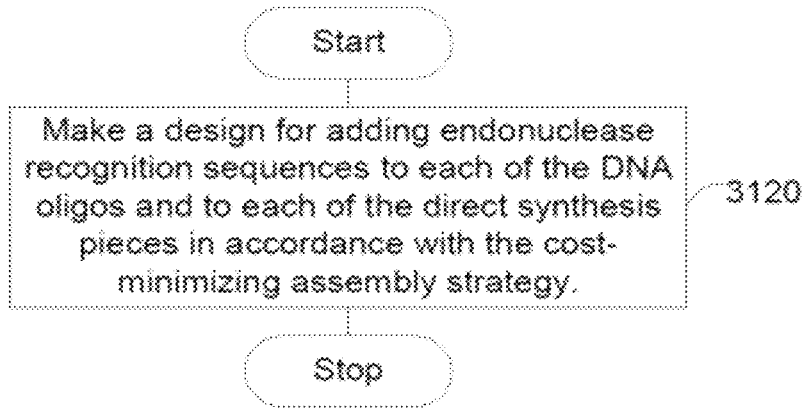
Figure 35C:
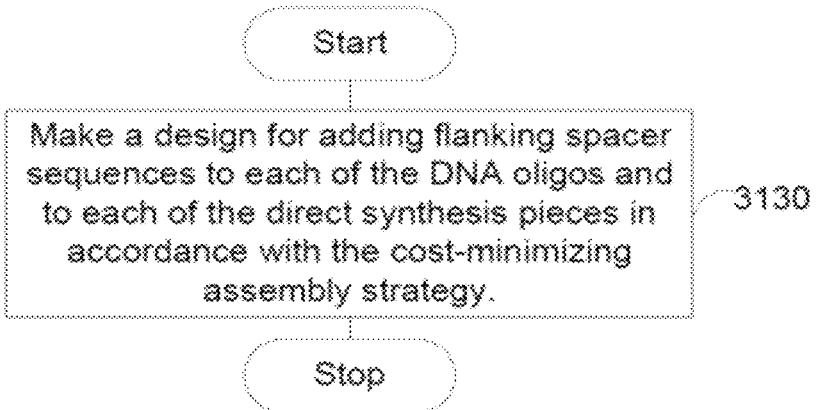

Referring to FIG. 35A, in an exemplary embodiment, creating step 2940 includes a step 3110 of planning the optimized overhang sequences with respect to a combinatorial library of DNA pieces. Referring to FIG. 35B, in an exemplary embodiment, creating step 2940 further includes a step 3120 of making a design for adding endonuclease recognition sequences to each of the DNA oligos and to each of the direct synthesis pieces in accordance with the cost-minimizing assembly strategy. Referring to FIG. 31C, in an exemplary embodiment, creating step 2940 further includes a step 3130 of making a design for adding flanking spacer sequences to each of the DNA oligos and to each of the direct synthesis pieces in accordance with the cost-minimizing assembly strategy.

Checking

Figure 36A:
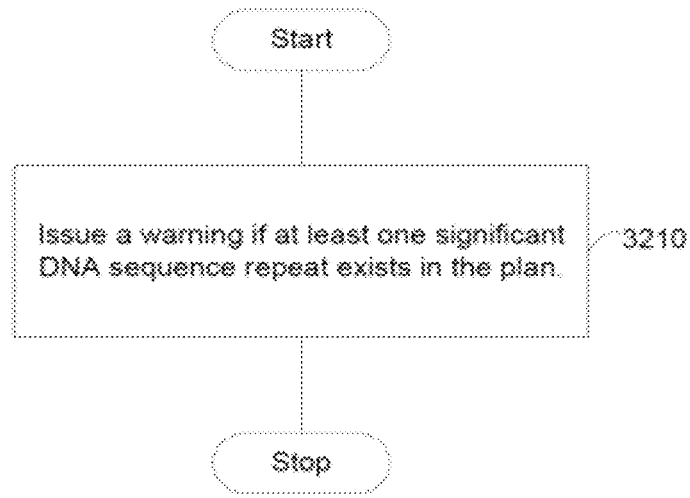
FIGS. 36A and 36B illustrate various components of one method used to design the DNA assembly process.
Figure 36B:
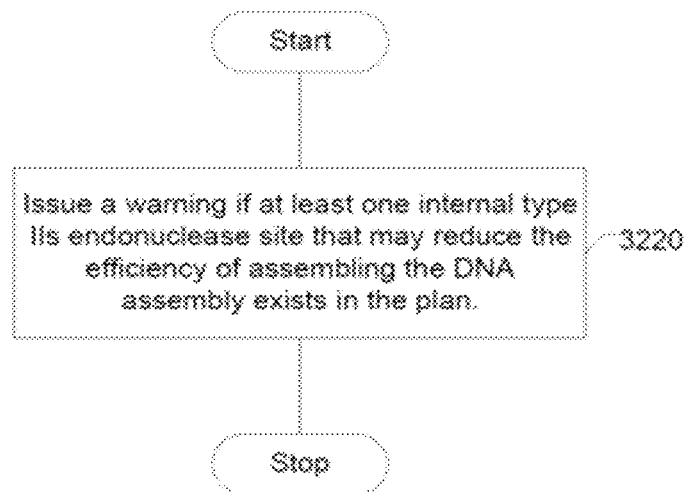

Referring to FIG. 36A, in an exemplary embodiment, checking step 2950 further includes a step 3210 of issuing a warning if at least one significant DNA sequence repeat exists in the plan. Referring to FIG. 36B, in an exemplary embodiment, checking step 2950 further includes a step 3220 of issuing a warning if at least one internal type Hs endonuclease site that may reduce the efficiency of assembling the DNA assembly exists in the plan.

Outputting

Figure 37A:
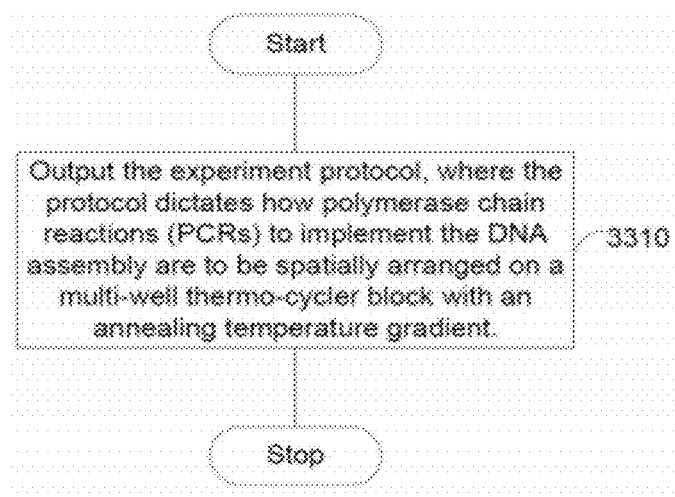
FIGS. 37A and 37B illustrate various components of one method used to design the DNA assembly process.
Figure 37B:
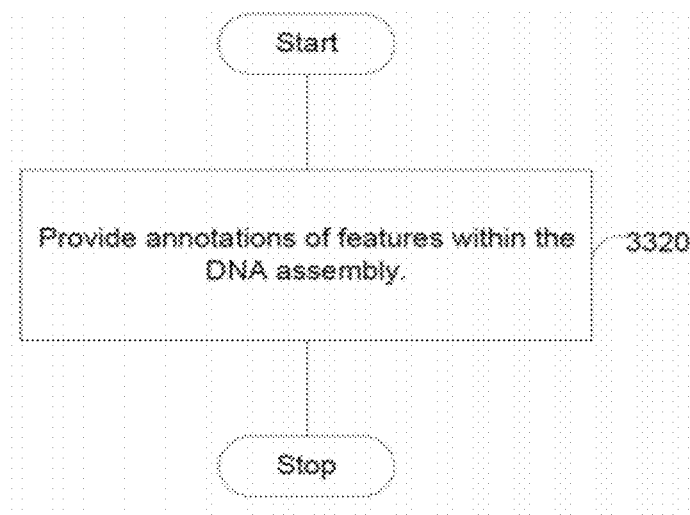

Referring to FIG. 37A, in an exemplary embodiment, outputting step 2960 includes a step 3310 of outputting the experiment protocol, where the protocol dictates how polymerase chain reactions (PCRs) to implement the DNA assembly are to be spatially arranged on a multi-well thermo-cycler block with an annealing temperature gradient. Referring to FIG. 37B, in an exemplary embodiment, outputting step 2960 further includes a step 3320 of providing annotations of features within the DNA assembly.

The foregoing assembly methods are intended to be illustrative and not limiting. Using the teachings provided herein many other assembly methods will be available to one of skill in the art.

Microfluidics Device (SynBioChip) Fabrication.

In various embodiments a microfluidics device, for the creation and reaction of various droplets in microfluid channels and/or chambers for the synthesis of various biological constructs (e.g. vectors comprising genes or combinations of genes, transformed cells, etc.), e.g., a SYNBIOCHIP®, is provided herein. In certain embodiments the microfluidic device comprises a plurality of channels for droplet formation and/or droplet mixing. In certain embodiments the microfluidic device comprises a plurality of microchambers for culturing cells.

In various embodiments, microchannels and/or microchambers comprising the devices described herein have a characteristic dimension (e.g. height or width or diameter) ranging from about 10 nm, or 100 nm, or 1 µm up to about 500 µm. In various embodiments the characteristic dimension ranges from about 1, 5, 10, 15, 20, 25, 35, 50, or 100 µm up to about 150, 200, 250, 300, or 400 µm. In certain embodiments the characteristic dimension ranges from about 20, 40, or about 50 µm up to about 100, 125, 150, 175 or 200 µm. In various embodiments the wall thickness between adjacent channels ranges from about 0.1 µm to about 50 µm, or about 1 µm to about 50 µm, more typically from about 5 µm to about 40 µm. In certain embodiments the wall thickness between adjacent channels ranges from about 5 µm to about 10, 15, 20, or 25 µm.

In various embodiments the channel depth ranges from 5, 10, 15, 20 µm to about 1 mm, 800 µm, 600 µm, 500 µm, 400 µm, 300 µm, 200 µm, 150 µm, 100 µm, 80 µm, 70 µm 60 µm, 50 µm, 40 µm, or about 30 µm. In certain embodiments the channel depth ranges from about 10 µm to about 60 µm, more preferably from about 20 µm to about 40 or 50 µm. In various embodiments the channels can be open or covered.

Where a nozzle/port is present, in various embodiments, the nozzle diameter ranges from about 0.1 µm, or about 1 µm up to about 300 µm, 200 µm, or about 100 µm, in certain embodiments from about 5, 10, 15, or 20 µm up to about 25, 30, 35, 40, 45, 50, 55, 60, 65, 70, 75, or 80 µm. In certain embodiments the nozzle diameter ranges from about 1, 5, 10, 15 or 20 µm up to about 25, 35, or 40 µm.

Suitable substrate materials include, but are not limited to transparent substrate such as polymers, plastics, glass, quartz, or other dielectric materials, nontransparent substrates including translucent or opaque plastics, silicon, metal, ceramic, and the like.

In various embodiments channel materials include, but are not limited to flexible polymers such as PDMS, plastics, and the like, and nonflexible materials such as stiff plastics, glass, silicon, quartz, metals, and the like.

There are many formats, materials, and size scales for constructing the microfluidic devices described herein and various integrated fluidic systems. In certain embodiments the devices described herein (including the microfluidic channels) are made of PDMS (or other polymers), fabricated using a technique called "soft lithography". PDMS is an attractive material for a variety of reasons including, but not limited to: (i) low cost; (ii) optical transparency; (iii) ease of molding; (iv) elastomeric character; (v) surface chemistry of oxidized PDMS can be controlled using conventional siloxane chemistry; (vi) compatible with cell culture (non-toxic, gas permeable). Soft lithographic rapid prototyping can be employed to fabricate the desired microfluidic channel systems.

One illustrative version of soft lithographic methods involves preparing a master (mold) (e.g., an SU-8 master) to form the microchannel system, pouring a pre-polymer onto the master and curing it to form a cured patterned replica (e.g., PDMS polymer replica), removing the replica from the master and trimming and punching tubing inlets as required, optionally exposing the polymer to a plasma (e.g., to an $O_2$ plasma) and optionally bonding the polymer to a substrate (e.g., a glass substrate).

Another useful property of PDMS and other polymers is that their surface can be chemically modified in order to obtain the interfacial properties of interest (see, e.g., Makamba et al. (2003) *Electrophoresis, i*24(21): 3607-3619). On illustrative method of covalently functionalizing PDMS is to expose it to an oxygen plasma, whereby surface Si—$CH_3$ groups along the PDMS backbone are transformed into Si—OH groups by the reactive oxygen species in the plasma. These silanol surfaces are easily transformed with alkoxysilanes to yield many different chemistries (see, e.g., *Silicon Compounds: Silanes and Silicones*, Gelest, Inc.: Morrisville, Pa., 2004; p. 560; Hermanson et al. (1992) *Immobilized affinity ligand techniques*, Academic Press, San Diego, Calif. 1992).

The master mold is typically a micromachined mold. Molds can be patterned by any of a number of methods known to those of skill in the in the electronics and micromachining industry. Such methods include, but are not limited to wet etching, electron-beam vacuum deposition, photolithography, plasma enhanced chemical vapor deposition (PECVD), molecular beam epitaxy, reactive ion etching (RIE), and/or chemically assisted ion beam milling (CAIBM techniques), and the like (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*, and the like).

Another illustrative micromachining method uses a high-resolution transparency film as a contact mask for a thick photoresist layer. Multilayer soft lithography improves on this approach by combining soft lithography with the capability to bond multiple patterned layers of elastomer. Basically, after separate curing of the layers, an upper layer is removed from its mold and placed on top of the lower layer, where it forms a hermetic seal. Further curing causes the two layers to irreversibly bond. This process creates a monolithic three-dimensionally patterned structure composed entirely of elastomer. Additional layers are added by simply repeating the process. The ease of producing multilayers makes it possible to have multiple layers of fluidics, a difficult task with conventional micromachining.

While the fabrication of the present devices is described with respect to the use of PDMS as a soft lithography material, it will be recognized that, in various embodiments, numerous other materials can be substituted for, or used in conjunction with PDMS. Illustrative materials include, but are not limited to polyolefin plastomers (POPs), perfluoropolyethylene (PFPE), polyurethane, polyimides, and cross-linked NOVOLAC® (phenol formaldehyde polymer) resins.

In various embodiments, single-layer or multi-layer PDMS (or other material) devices are contemplated. In illustrative approach, a network of microfluidic channels is designed in a CAD program. This design is converted into a transparency by a high-resolution printer; this transparency is used as a mask in photolithography to create a master in positive relief photoresist. PDMS cast against the master yields a polymeric replica containing a network of channels. The surface of this replica, and that of a flat slab of PDMS, can be oxidized in an oxygen plasma. These oxidized surfaces seal tightly and irreversibly when brought into conformal contact. Oxidized PDMS also seals irreversibly to other materials used in microfluidic systems, such as glass, silicon, silicon oxide, and oxidized polystyrene. Oxidation of the PDMS has the additional advantage that it yields channels whose walls are negatively charged when in contact with neutral and basic aqueous solutions; these channels support electroosmotic pumping and can be filled easily with liquids with high surface energies (especially water).

In certain illustrative embodiments the microfluidic chips are fabricated by patterning channels and valves in poly (dimethylsiloxane) (PDMS) using conventional soft lithography methods. Briefly, SU8-2025 photoresist (MicroChem. Corp.) is spin-coated onto silicon wafers and patterned by UV exposure contact mask aligner through a photolithography mylar mask and subsequent development (SU-8 developer; MicroChem Corp.). Then two mixtures (20:1 and 5:1 (w/w)) of Sylgard 184 silicone elastomer and curing agent (Dow Corning Corp), degassed under vacuum, was poured onto two silicon wafers with channels and valves patterns, respectively, and cure at 80° C. for 1 hour. Then, the channel-structured PDMS layer is peeled from the master and then aligns with the valve layer and cure at 80° C. for another 1 hour. After curing, the bonded two-layer structure is peeled off the silicon wafer and input/output ports were punched out of the PDMS with a 0.75 mm-diameter Uni-Core punch. Finally, the structured side of the PDMS piece was brought into conformal contact with a glass slide treated with oxygen plasma.

The fabrication methods described herein are illustrative and not limiting. Using the teachings provided herein, numerous other photolithographic and/or micromachining techniques can be used to fabricate the devices described herein. The micromachining and soft lithography methods described above, as well as many others, are well known to those of skill in the art (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*; McDonald et al. (2000) *Electrophoresis*, 21(1): 27-40).

EXAMPLES

The following examples are offered to illustrate, but not to limit the claimed invention.

Example 1

SYNBIOCHIP® Microfluidic Platform

Figure 39A:
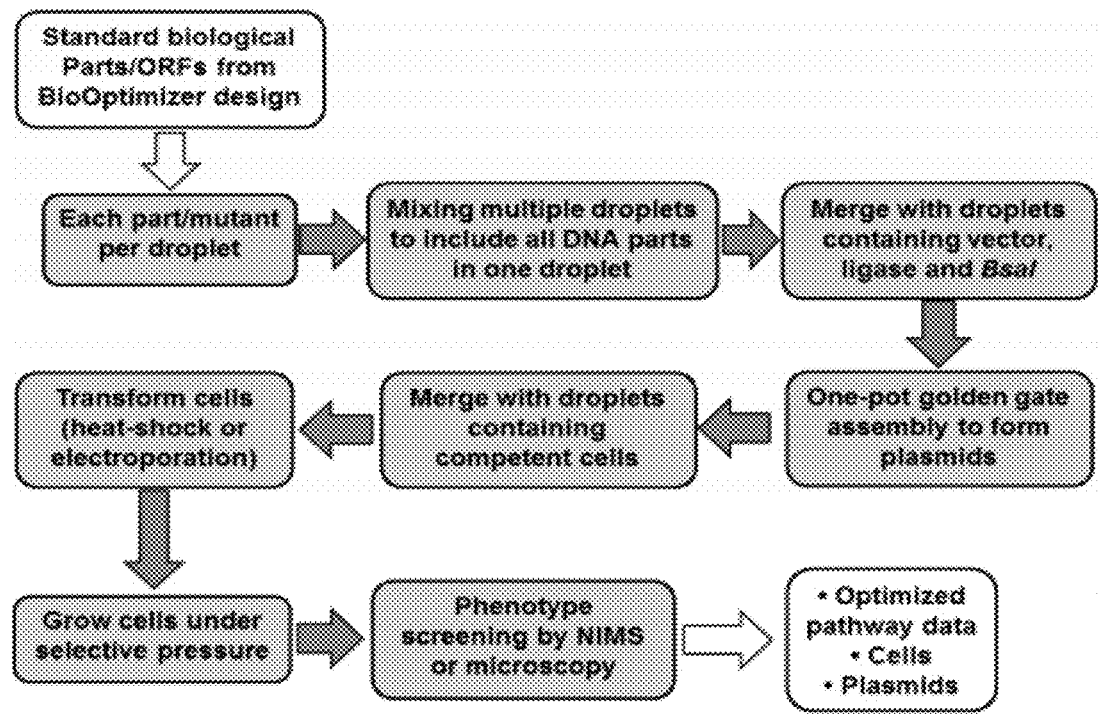
FIG. 39A illustrates certain unit operations to be performed in a SynBioChip. White boxes and arrows depict input and output from the SynBioChip. Shaded boxes and arrows depict functional steps that are performed on-chip.
Figure 39B:
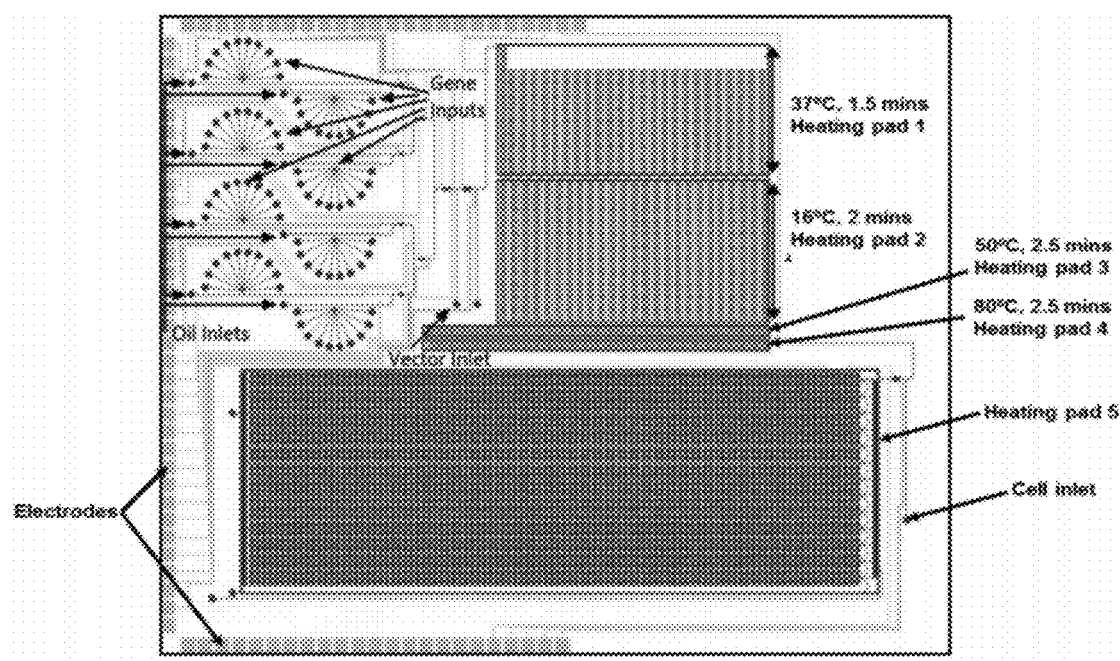
FIG. 39B illustrates a SynBioChip for gene assembly, transformation, cell culture and fluorescence imaging readout. Synthesized genes or other parts are introduced in the inlets. They are encapsulated in water-in-oil droplets (or buffer-in-oil droplets) and then merged on-demand using electrocoalescence (electrodes). The borders surrounding the incubation chambers and serpentine sections indicate 5 different heating pads (heating pads 1-5).

The heat of the integrated system(s) described herein is a microfluidic chip that enables thousands of reactions in parallel using nL droplets as reaction vessels. Droplets are created by dispensing aqueous solution carrying biological parts into an oil stream. The chip allows on-demand creation and merger of droplets to permit assembly of DNA into plasmids, transformation of cells, culture of transformed cells, and subsequent phenotype screening. FIG. 39A shows a schematic of the operations performed in a SYNBIO-CHIP® and FIG. 39B shows a drawing of the chip.

Chip Fabrication.

Chips are fabricated by standard photolithography process described in many of our publications (see, e.g., Throckmorton (2002) *Anal. Chem.*, 74: 784-789). To allow for structural rigidity while keeping the ability to easily clean the chip for reuse and macroscopic analysis, a thin PDMS layer sandwiched by two quartz wafers can be utilized. The bottom wafer contains all the etch channel features and patterned electrodes, while the top wafer contains the access holes for fluid delivery. The thin PDMS layer is spin casted onto the top holes-wafer, making for more efficient bonding of the two wafers and the ability to separate after use.

Introduction of Biological Parts:

Following assembly process design (e.g., using the methods described above and/or in application no. 61/438,601, the user can purchase the DNA oligonucleotides and direct DNA synthesis services required for the assembly, and perform the requisite digests and/or PCR reactions. Thereafter, multi-well plate(s) containing the resulting DNA parts to assemble, along with reservoirs of Golden-gate assembly reagents and competent *E. coli* cells, would be connected to the microfluidic device. As shown in FIG. 39B, the genes and their variants are introduced in reservoirs mounted on top of the SynBioChip.

Encapsulation of Genes in Droplets.

Figure 40A:
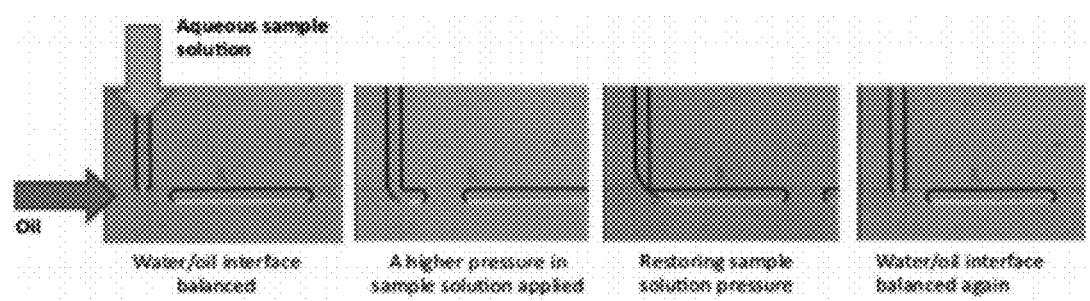
FIGS. 40A and 40B show time-lapse photos showing droplet generation (~2 µL in volume) (FIG. 40A) and droplets generated (FIG. 40B) with different contents.
Figure 40B:
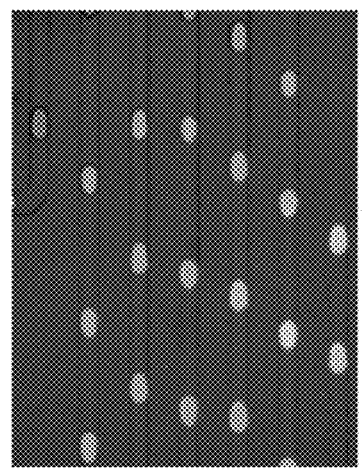

Droplets are generated by mixing water (or buffer and the like) and oil streams at a junction with DNA parts and other molecular biology reagents being carried in the water stream. By adjusting one inlet pressure significantly higher than the others, a particular gene variant can be selected to flow to the droplet generation junction. Droplet size, spacing, and transportation speed can be adjusted by fine-tuning the ratio of water to oil flow rate. Droplet generation can be in either continuous or on-demand mode. Here we prefer generating droplets on-demand as this will help make sure all droplets are mixing in a desired manner without any errors. This process has been optimized and FIGS. 40A and 40B show an example of droplets generated in the chip.

A 3.4 Gene Assembly

Figure 41A:
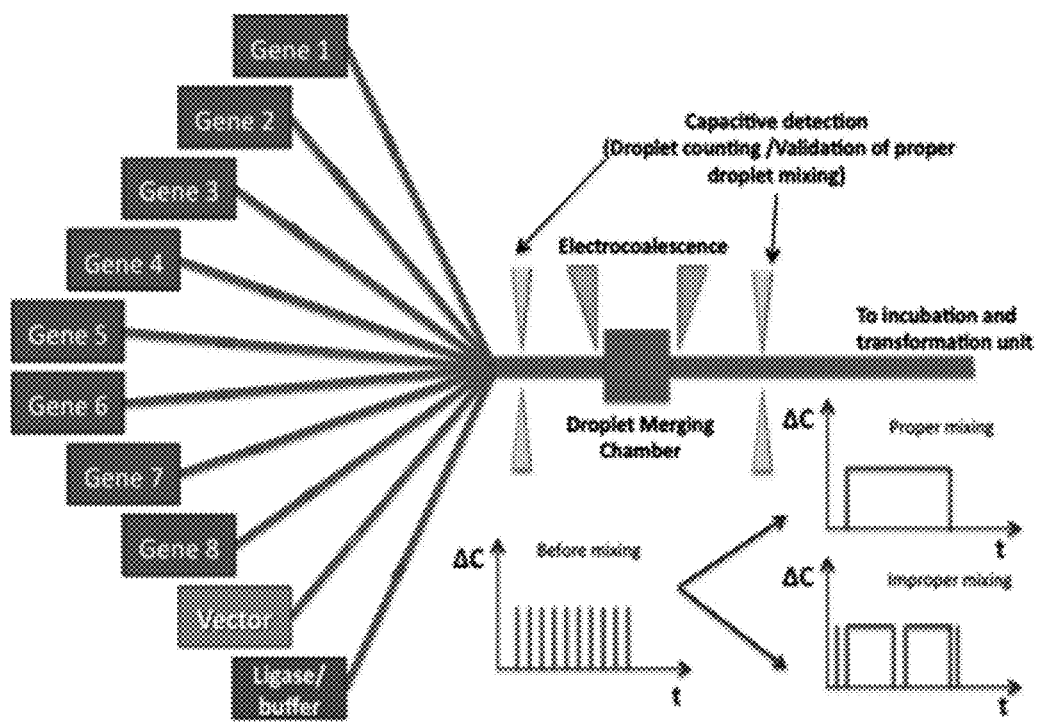
FIGS. 41A and 41B show a schematic of droplet generation, merging and tracking (FIG. 41A) and time-lapse photos showing droplet merging by electrocoalescence. High-resolution capacitive measurement allows detection of droplets together with assessing whether droplets were properly merged.
Figure 41B:
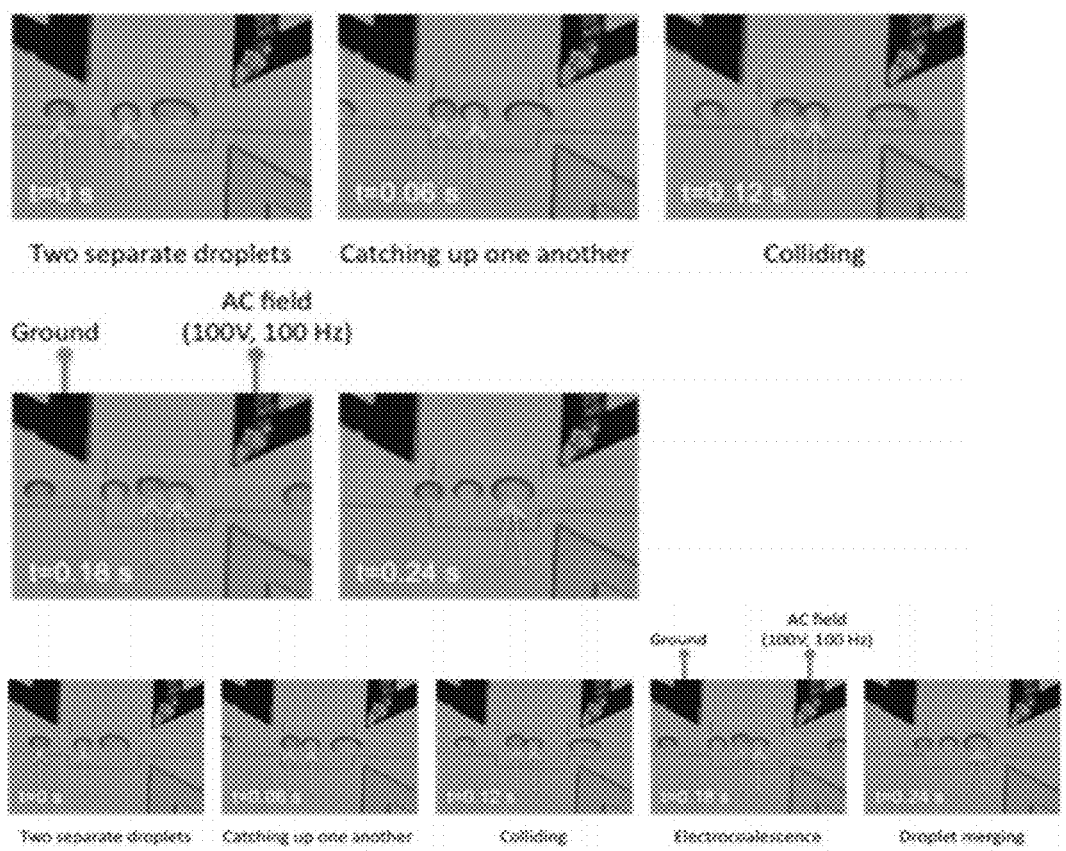

A particular gene combination is formed by individually selecting one gene variant from each gene library, along with vector, ligase, buffer, and other reagents. Two droplets are merged by electrocoalescence as shown in FIGS. 41A and 41B. Two pairs of capacitive detection electrodes can be placed before and after the droplet merging chamber to validate proper droplet merging. Once all the droplets are correctly mixed to form one droplet, it is delivered. Droplets from each gene (or variant) are combined with every other gene (or variant) and then combined with droplets that contain the linearized vector, BsaI restriction enzyme, ligase and appropriate buffers. At this point, each droplet has all the components necessary for golden-gate assembly and each droplet has a unique combination of genes.

Assembly of the different parts on-chip can be achieved by the standard protocols used for the one-pot golden gate assembly method. After each droplet containing the specified gene variants and vector have mixed into one, it enters a long serpentine channel that directs the droplet over 4 heating pads at temperatures of, e.g., 16° C., 37° C., 50° C. and 80° C. The topography of the serpentine channel is arranged so that the droplet experiences a cycle of temperatures for a controlled amount of time determined by channel length and fluid velocity. In certain embodiments the chip uses a modified Golden Gate protocol where each drop spends 1.5 minutes at 37° C., followed by 2 minutes at 16° C. This cycle repeats 25 times. The droplet then is heated to 50° C. for 2.5 minutes, followed by 80° C. for an additional 2.5 minutes with no repetition. The droplet is then combined with a droplet containing *E. coli* where it is transformed and directed to the incubation chambers.

Transformation

Two methods are readily used for on-chip transformation of plasmids into cells; heat shock and electroporation. Heat shock involves a heat cycle on the entire chip or small portion. An illustrative heat cycle is 4° C. for 30 minutes, bring up to 42° C. for 1 minute, cool back down to 4° C. for 5 minutes then carry on the remaining chip operation at 37° C. Alternatively, an on-chip electroporation method can be utilized involving plating of electrodes onto the channel surface, and applying an electric field across the droplet as it passes by. This method has several advantages over heat shock, simplifying chip design and process, and preventing any protein denaturation due to heat fluctuation.

Cell Culture.

Figure 42:
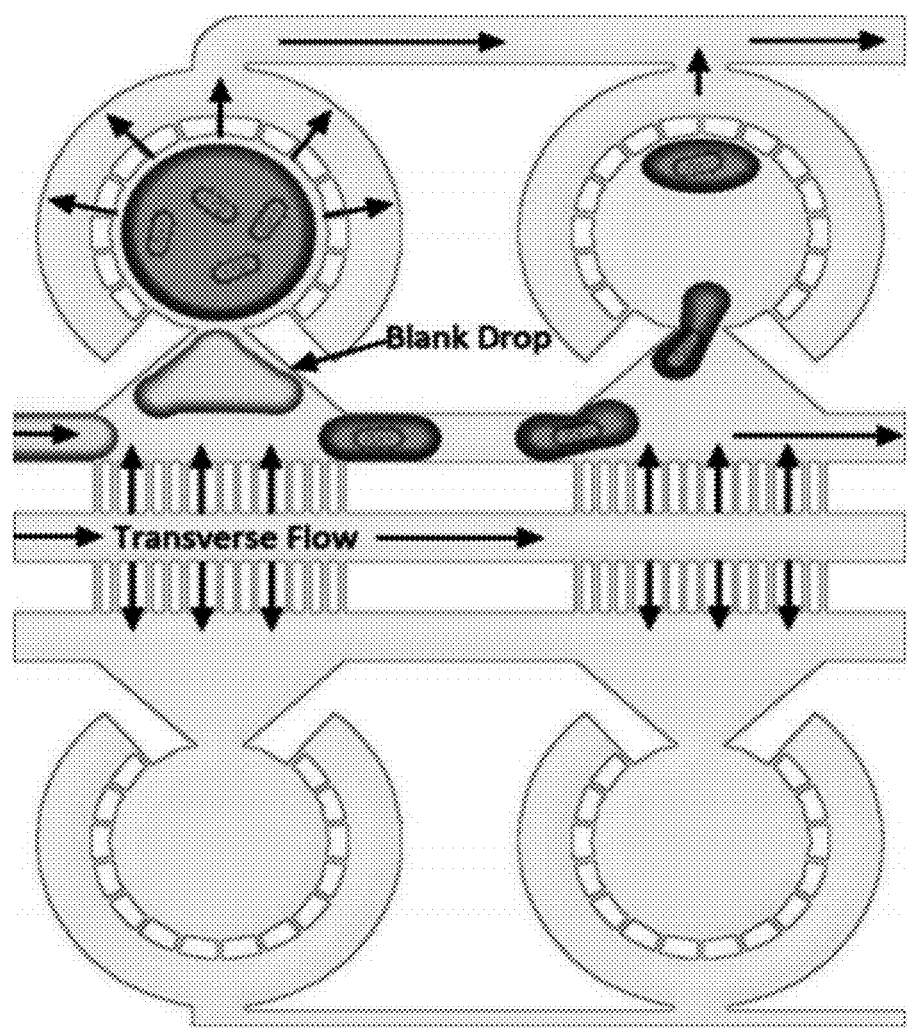
FIG. 42 shows a diagram of a small section of the incubation section of the chip. The top left chamber has already been filled, allowing the next droplets to pass, where the transverse flow pushes droplets into the next chamber. Once all chambers are filled, aqueous flow containing nutrients replaces the oil phase, exiting through small perfusion chambers that do not allow the cells to leave due to size exclusion.

To take advantage of the ability of mass parallelization that is inherent to microfluidics, droplets containing cells with different gene variants can fill separate on-chip incubation chambers (FIG. 42). Each chip contains 10,000 individual chambers each holding an approximate volume of 5 nL. There are two steps for long-term cell culture-chamber filling and nutrient supply. Each chamber is first filled with aqueous droplets containing transformed *E. coli* cells, using the applied transverse flow to direct droplets into the incubation chambers. To ensure that only one type of gene variant occupies each chamber, each combination of droplets containing plasmids and cells can be made to have a volume equal to that of an incubation chamber. Once a chamber cannot hold anymore droplets, the next droplet passes over and fills the next chamber (FIG. 42), until each chamber is completely filled with cells containing different gene variants.

Once the desired number of chambers are filled, the upstream oil flow is switched to an aqueous solution containing nutrients necessary for the cells to proliferate. At this stage all flow is aqueous. Once all oil has been pushed out by the aqueous nutrient solution, the cells continue to remain in the chamber due to small 'perfusion channels' that surround each incubation chamber (see FIG. 42). These perfusion channels are etched at a lesser depth than the rest of the device, with dimensions of 500 nm deep by 10 µm wide. These perfusion channels allow constant refreshing of nutrients while keeping cells in the chamber. Once the chambers are filled, the cells are allowed to grow in these chambers at, e.g., 37° C.

In certain embodiments the SYNBIOCHIP® experiment is performed in 2-stages: In stage 1 DNA assembly is performed, cells are transformed and cultured for ~1 hr. In stage 2 the chip is removed from the droplet generation setup and moved to a simpler setup and maintained at, e.g., 37° C. where just one input is connected to the chip to enable long-term cell culture by constant media perfusion. Once the first chip is removed from the droplet generation setup, a second chip can be mounted to perform another 10,000 reactions. Thus, 10 chips run on the same setup, staggered by ~2.5 hrs, in a 24-hr period.

Capacitive Detection of Droplets in Microfluidic Channel:

In certain embodiments the presence, size and speed of droplets in microfluidic channel can be detected by using commercially available capacitive sensors which make the droplet-based microfluidic systems scalable and inexpensive. Cross-contamination between the droplets could be eliminated by introducing a passivation layer between the sensing electrodes and droplets. Coplanar electrodes are used to form a capacitance through the microfluidic channel. The change in capacitance due to the presence of a droplet in the sensing area is detected and used to determine the size and speed of the droplet. The design of a single pair of electrodes can be used to detect the presence of a droplet and the interdigital finger design can be used to detect the size and speed of the droplet. The measured droplet information can be displayed through a LabVIEW interface in real-time.

Imaging Data Collection and Analysis:

Each chamber has fresh nutrients flowing through for the entire incubation time, during which the cell growth and signal (usually fluorescence) can be monitored. An automated stage mounted to a microscope with a CCD camera can be used to rapidly collect and analyze each chamber. Stage operation can be operated via LABVIEW®, with all image data analysis done with MATLAB®.

Systems Engineering

A complex microfluidic platform such as SYNBIOCHIP® involves seamless integration of the chip with external components, both hardware and software, for optimal implementation. The integration of the various microfluidic system components can be centered on utilizing a standard imaging microscope. The microfluidic components, manifold with peripheral hardware, and reagent cartridges can be attached to a platen compatible with standard microscopes. In certain embodiments the system controller will reside near the microscope connected to the platen manifold via a single umbilical that provides the pneumatic driving pressures for the fluids, electrical signals to cue the valves to actuate, and HV voltage lines for CCD imager. A laptop PC can be used to drive all components using customized LABVIEW® interfaces with flexible and automated multi-step control options and built-in data collection. A number of programs have been developed to control different components (e.g., temperature control, flow control for generating droplets etc.). Several advancements can be implemented to the platform to improve the overall stability and reproducibility of the system. In particular, on-chip temperature controls and sensors for droplet tracking can be optimized.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of assembling a biological construct, said method comprising:
encapsulating a plurality of separate components of said biological construct in discrete and separate fluid droplets to provide different components of said construct each in different discrete fluid droplets, where said discrete fluid droplets are disposed in an immiscible fluid that separates said droplets, where a plurality of discrete fluid droplets containing the same type of component are in a single fluid channel containing said immiscible fluid and a plurality of single fluid channels are disposed in a microfluidics device to provide a microfluidics device comprising different fluid channels where each fluid channel contains a plurality of discrete fluid droplets each containing the same type of component and the fluid droplets in different fluid channels contain different components;
introducing fluid droplets from said different fluid channels of said device into a common channel of said device in fluid communication with said plurality of fluid channels to form a spatially sequenced order of separate discrete fluid droplets in an immiscible fluid inside said common channel where different droplets comprising said spatially sequenced order of discrete fluid droplets contain said different components; and
moving the immiscible fluid containing said separate discrete fluid droplets along said common channel and into a droplet merging channel in fluid communication with said common channel to combine two or more fluid droplets of said spatially sequenced order of fluid droplets into a common droplet in said immiscible fluid and to react said separate components with each other in one or more reactions that assemble said separate components together to form said biological construct.

2. The method of claim 1, wherein said separate components of said biological construct comprise components independently selected from the group consisting of a promoter, a terminator, a secretion signal, a gene, a vector, and a cell.

3. The method of claim 2, wherein said separate components each contain an element independently selected from the group consisting of a promoter, a terminator, a secretion signal, a gene, and a vector, and said combining two or more fluid droplets of said sequenced order of fluid droplets to react said separate components with each other comprises combining two or more fluid droplets wherein at least one of said fluid droplets further contains a restriction enzyme whereby said combining performs a restriction digest reaction in the combined fluid droplets.

4. The method of claim 1, wherein said separate components of said biological construct comprise genes and different fluid droplets comprising said sequenced order of fluid droplets contain different genes.

5. The method of claim 4, wherein said combining two or more fluid droplets of said sequenced order of fluid droplets to react said separate components with each other comprises combining two or more fluid droplets wherein at least one of said two or more fluid droplets further contains a ligase whereby said combining performs a ligation of said different genes to each other in the combined fluid droplets.

6. The method of claim 1, wherein said combining two or more fluid droplets of said sequenced order of fluid droplets to react said separate components with each other comprises combining two or more fluid droplets wherein at least one of said two or more fluid droplets further contains a ligase whereby said combining performs a ligation of a plurality of genes together under the control of a promoter in the combined fluid droplets.

7. The method of claim 1, wherein said combining two or more fluid droplets of said sequenced order of fluid droplets to react said separate components with each other comprises combining two or more fluid droplets, wherein at least one of said two or more fluid droplets further contains a vector and said combining introduces said components into said vector.

8. The method of claim 7, wherein said vector is a plasmid or cosmid.

9. The method of claim 1, wherein said combining two or more fluid droplets of said sequenced order of fluid droplets to react said separate components with each other comprises combining two or more fluid droplets to assemble a nucleic acid construct using constructs selected from the group consisting of DNA sequences that conform to a restriction-enzyme assembly standard, constructs for sequence and ligation independent cloning (SLIC), constructs configured for the joining of multiple DNA fragments in a single, isothermal reaction, constructs for circular polymerase extension cloning (CPEC), and constructs incorporating a recognition site for a single type IIS restriction enzyme and a T4 DNA ligase.

10. The method of claim 1, wherein said combining two or more fluid droplets of said sequenced order of fluid droplets to react said separate components with each other comprises combining two or more fluid droplets, wherein at least one of said two or more fluid droplets further contains a cell and said combining introduces a nucleic acid construct into said cell.

11. The method of claim 10, wherein said cell is selected from the group consisting of a bacterial cell, a mammalian cell, an insect cell, a plant cell, an algal cell, and a fungal cell.

12. The method of claim 10, wherein said method further comprises identifying and capturing and/or trapping a cell containing said construct.

13. The method of claim 1, wherein said immiscible fluid comprises an oil.

* * * * *